(12) United States Patent
Bradner et al.

(10) Patent No.: US 10,934,256 B2
(45) Date of Patent: Mar. 2, 2021

(54) COMPOUNDS AND METHODS FOR TREATING CANCER

(71) Applicant: Dana-Farber Cancer Institute, Inc., Boston, MA (US)

(72) Inventors: James Bradner, Weston, MA (US); Michael Erb, Boston, MA (US); Jun Qi, Sharon, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 0 days.

(21) Appl. No.: 16/575,733

(22) Filed: Sep. 19, 2019

(65) Prior Publication Data

US 2020/0010418 A1 Jan. 9, 2020

Related U.S. Application Data

(62) Division of application No. 15/577,845, filed as application No. PCT/US2016/035641 on Jun. 3, 2016, now Pat. No. 10,464,897.

(60) Provisional application No. 62/171,783, filed on Jun. 5, 2015.

(51) Int. Cl.
| | |
|---|---|
| C07D 211/44 | (2006.01) |
| C07D 401/14 | (2006.01) |
| C07D 401/04 | (2006.01) |
| C07D 413/04 | (2006.01) |
| C07D 239/78 | (2006.01) |
| C07D 471/04 | (2006.01) |
| C07D 211/58 | (2006.01) |
| C07D 213/30 | (2006.01) |
| A61P 35/00 | (2006.01) |

(52) U.S. Cl.
CPC ............ *C07D 211/44* (2013.01); *A61P 35/00* (2018.01); *C07D 211/58* (2013.01); *C07D 213/30* (2013.01); *C07D 239/78* (2013.01); *C07D 401/04* (2013.01); *C07D 401/14* (2013.01); *C07D 413/04* (2013.01); *C07D 471/04* (2013.01)

(58) Field of Classification Search
CPC .. C07D 211/44; C07D 211/58; C07D 213/30; C07D 239/78; C07D 401/04; C07D 401/14; C07D 413/04; C07D 471/04; A61P 35/00
USPC ........................................................ 514/403
See application file for complete search history.

(56) References Cited

U.S. PATENT DOCUMENTS

| | | | | |
|---|---|---|---|---|
| 3,957,813 A | * | 5/1976 | Irick, Jr. ............ | C07D 209/18 548/224 |
| 6,613,245 B1 | | 9/2003 | Ohlemacher | |
| 10,464,897 B2 | * | 11/2019 | Bradner ............... | C07D 401/14 |
| 2006/0063779 A1 | | 3/2006 | Gunzner | |
| 2009/0281089 A1 | | 11/2009 | Gunzner | |
| 2012/0196849 A1 | * | 8/2012 | Gao ....................... | C07C 235/56 514/211.15 |
| 2012/0282259 A1 | | 11/2012 | De Sauvage et al. | |
| 2015/0038563 A1 | | 2/2015 | Fournier | |

FOREIGN PATENT DOCUMENTS

| | | | | |
|---|---|---|---|---|
| WO | 2003051876 | | 6/2003 | |
| WO | 2005033288 | A2 | 10/2008 | |
| WO | 2008131354 | A2 | 10/2008 | |
| WO | 2013153330 | A2 | 10/2013 | |
| WO | 2014191737 | A1 | 12/2014 | |
| WO | WO-2015034271 | A1 * | 3/2015 | ............. A61P 31/10 |
| WO | WO-2015148300 | A1 * | 10/2015 | |
| WO | 2018121610 | A1 | 7/2018 | |

OTHER PUBLICATIONS

National Center for Biotechnology Information. PubChem Database. CID=69955422, Create Date Dec. 1, 2012 https://pubchem.ncbi.nlm.nih.gov/compound/69955422 (accessed on Jun. 4, 2020) (Year: 2012).*
Pan; ACS Med. Chem. Lett. 2010, 1, 3, 130-134. doi: 10.1021/ml1000307 (Year: 2010).*
Lin; Onco Targets Ther. 2012, 5, 47-58. (Year: 2012).*
Amakye et al., "Unraveling the therapeutic potential of the Hedgehog pathway in cancer", Nat. Med., vol. 19, No. 11, pp. 1410-1422 (2013).
CAS RN 505062-42-0 (Apr. 25, 2003).
CAS RN 1714223-13-8 (May 28, 2015).
CAS RN 101418-16-0 (Apr. 12, 1986).
CAS RN 200417-27-2 (Jan. 29, 1998).
CAS RN 200417-29-4 (Jan. 29, 1998).
CAS RN 294851-47-1 (Oct. 12, 2000).
CAS RN 503427-52-9 (Apr. 18, 2003).
CAS RN 503427-53-0 (Apr. 18, 2003).
CAS RN 850801-19-3 (May 20, 2005).
CAS RN 1477819-91-2 (Nov. 21, 2013).
Chemical Abstracts, STN record for RN 946409-33-2, entered on Sep. 7, 2007. (Year: 2007).
Gong et al., "A novel phenylimidazo[1,2-a]pyridine core and pharmacophore model as hypoxia-inducible factor inhibitors", Bull. Korean Chem. Soc., vol. 31, No. 7, pp. 2039-2042 (2010).
Gorlin, "Nevoid basal cell carcinoma (Gorlin) syndrome", Genet. Med., vol. 6, No. 6, pp. 530-539 (2004).
Hoff et al., "Inhibition of the hedgehog pathway in advanced basal-cell carcinoma", N. Engl. J. Med., vol. 361, No. 12, pp. 1164-1172 (2009).

(Continued)

*Primary Examiner* — Daniel R Carcanague
(74) *Attorney, Agent, or Firm* — Burns & Levinson, LLP; Daniel W. Clarke

(57) ABSTRACT

The present application relates to compounds comprising an ester, a thioester, or a hydrazide moiety and methods of synthesizing these compounds. The present application also relates to pharmaceutical compositions containing the compounds and methods of treating cell proliferative disorders mediated by the Hh signaling pathway, such as cancer, by administering the compounds and pharmaceutical compositions to subjects in need thereof.

18 Claims, 10 Drawing Sheets

(56) References Cited

OTHER PUBLICATIONS

Robarge et al., "GDC-0449—a potent inhibitor of the hedgehog pathway", Bioorg. Med. Chem. Lett., vol. 19, No. 19, pp. 5576-5581 (2009).

Santra et al., "Ceric ammonium nitrate (CAN) promoted Pd(II)-catalyzed substrate-directed o-benzoxylation and decarboxylative o-aroylation", Eur. J. Org. Chem., vol. 2015, No. 2, pp. 350-356.

Sharpe et al., "Regulation of the oncoprotein smoothened by small molecules", Nat. Chem. Biol., vol. 11, No. 4, pp. 246-255 (2015).

Tang et al. "Inhibiting the hedgehog pathway in patients with the basal-cell nevus syndrome", N. Engl. J. Medi., vol. 366, p. 2180-2188 (2012).

Testa; Chapter 7, "The Hydrolysis of Carboxylic Acid Esters", in Hydrolysis in Drug and Prodrug Metabolism, Verlag, Zurich, 2003, pp. 365-418. (Year: 2003).

\* cited by examiner

COMPOUNDS AND METHODS FOR TREATING CANCER

RELATED APPLICATIONS

This application is a divisional application of U.S. application Ser. No. 15/577,845, now allowed, which is a U.S. National Phase application, filed under 35 U.S.C. § 371, of International Application No. PCT/US2016/035641, filed on Jun. 3, 2016, which claims priority to, and the benefit of U.S. Provisional Application No. 62/171,783, filed on Jun. 5, 2015, the contents of each of which are incorporated herein by reference in their entireties.

BACKGROUND

Aberrant regulation of the Hedgehog (Hh) signaling pathway drives several cancers, including medulloblastoma (MB) and Basal Cell Carcinoma (BCC), and is often caused by mutations to Patched (PTCH) or Smoothened (SMO) (Amakye et al., Nat. Med. 19, 1410 (2013)). Loss of function mutations to PTCH in the germline are responsible for Gorlin syndrome (also known as nevoid basal cell carcinoma syndrome, NBCCS), a serious genetic disorder that predisposes an individual to several forms of cancer, including MB and BCC (Gorlin, Genet. Med. 6, 530 (2004)). Fortunately, SMO has proved extensively receptive to regulation by small molecules (Sharpe et al., Nat. Chem. Biol. 11, 246 (2015)).

SMO is a GPCR-like molecule whose activity can be modulated by various small molecules, including several currently under clinical investigation for Hedgehog-related pathologies. Although SMO transduces the Hedgehog signal across the cell membrane, Hedgehog ligands actually bind and inactivate the transporter like molecule PTCH, which functions as a tumor suppressor and represses the activity of SMO. Vismodegib, a SMO antagonist, has been approved for the treatment of locally advanced and metastatic BCC since 2012 (Hoff et al., New Eng. J. Med. 361, 1164 (2009), Sharpe et al., 2015). However, in a Phase II study of vismodegib in patients with NBCCS, over half (14 of 26) of the participants ceased treatment due to serious adverse effects (Tang et al., New Eng. J. Med. 366, 2180 (2012)). Accordingly, new compounds and methods for treating proliferation disorders mediated by the Hh signaling pathway, including cancer, are needed. The present application addresses these needs.

In order to increase the therapeutic index of SMO antagonism as a treatment for BCC, retrometabolic (soft) drug design is employed in the development of novel SMO antagonists. In retrometabolic drug design, metabolic reaction information is used to design drugs whose metabolism and distribution can be controlled to target and eliminate the drug to increase efficacy and minimize undesirable side effects. These approaches represent systematic methodologies that thoroughly integrate structure-activity (SAR) and structure-metabolism (SMR) relationships and are aimed at designing safe, locally active compounds with improved therapeutic index (ratio of benefit vs. side effect). For example, inclusion of ester functionality into the compounds creates SMO antagonists with a liability to serum esterases, which enables rapid metabolic inactivation of the drug in the bloodstream. Also, topical treatment with such compounds will provide high therapeutic concentrations local to the site of application while avoiding systemic effects.

SUMMARY

The present application provides compounds comprising an ester moiety (i.e., C(O)O), a thioester moiety (i.e., C(O)S), or a hydrazide moiety (i.e., C(O)NH—NH), and methods for treating disorders mediated by the Hh signaling pathway. Specifically, the present application provides a compound of formula A:

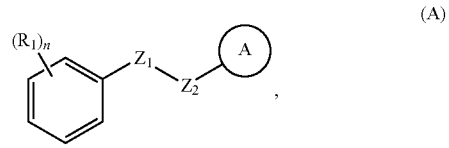

or a pharmaceutically acceptable salt thereof, wherein $R_1$, $Z_1$, $Z_2$, and n are each defined herein and can each be selected from the respective groups of chemical moieties disclosed herein in the detailed description.

The present application also provides pharmaceutical compositions comprising one or more compounds of any of the formulae described herein or a pharmaceutically acceptable salt thereof, and one or more pharmaceutically acceptable carriers.

The present application also provides topical compositions comprising one or more compounds of any of the formulae described herein or a pharmaceutically acceptable salt thereof, and one or more pharmaceutically acceptable carriers.

The present application also provides methods of modulating the SMO, comprising contacting the SMO with a compound of the any of the formulae described herein or a pharmaceutically acceptable salt thereof.

The present application also provides methods of treating a disorder mediated by the Hh signaling pathway, by administering to a subject in need thereof, a therapeutically effective amount of a compound of any of the formulae described herein, or a pharmaceutically acceptable salt thereof, in combination with a pharmaceutically acceptable carrier, such that the disorder is treated.

The present application also provides methods of treating a cell proliferative disorder mediated by the Hh signaling pathway, by administering to a subject in need thereof, a therapeutically effective amount of a compound of any of the formulae described herein, or a pharmaceutically acceptable salt thereof, in combination with a pharmaceutically acceptable carrier, such that the disorder is treated.

The present application also provides methods of treating cancer mediated by the Hh signaling pathway, by administering to a subject in need thereof, a therapeutically effective amount of a compound of any of the formulae described herein, or a pharmaceutically acceptable salt thereof, in combination with a pharmaceutically acceptable carrier, such that the cancer is treated.

The present application also relates to use of a compound of any of the formulae described herein, or a pharmaceutically acceptable salt thereof for the treatment of a disorder, a cell proliferative disorder, or a cancer mediated by the Hh signaling pathway.

The present application also relates to use of a compound of any of the formulae described herein, or a pharmaceutically acceptable salt thereof, in the manufacture of a medicament for the treatment of a disorder, a cell proliferative disorder, or a cancer mediated by the Hh signaling pathway.

The present application provides methods of synthesizing compounds of each of the formulae described herein, or pharmaceutically acceptable salts thereof.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the application will be apparent from the following detailed description and claims.

DETAILED DESCRIPTION

1. Compounds of the Present Application

Figure 1:
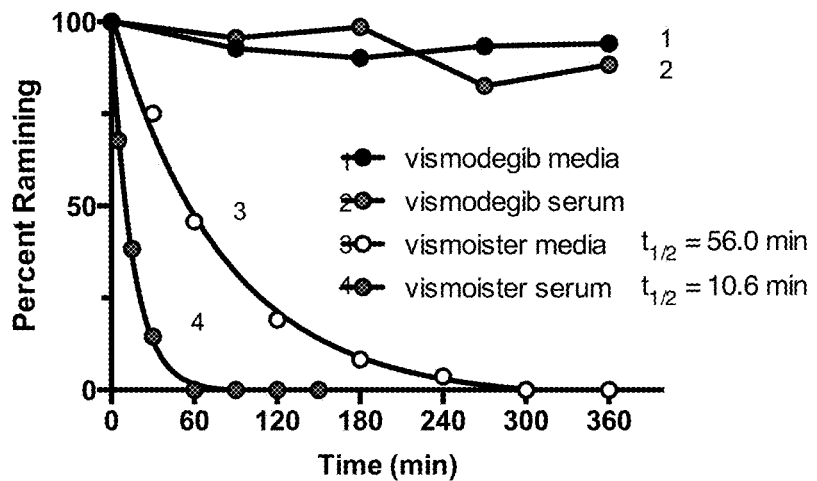
FIG. 1: top panel: a graph showing the amount of the indicated compounds incubated at 37° C. in serum-free media or serum over time; bottom panel: a graph showing the amount of vismoister incubated at 37° C. in serum-free media or serum over time.
Figure 1:
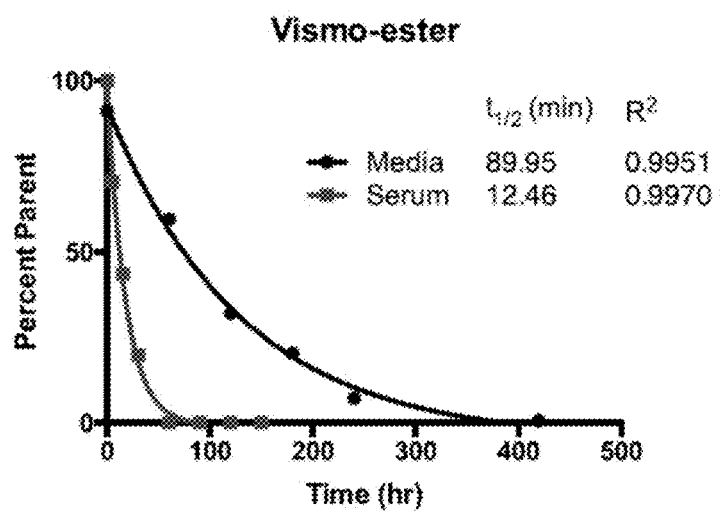

The present application provides compounds or pharmaceutically acceptable salts thereof, pharmaceutical compositions (e.g., topical formulations) containing them, and various uses of the disclosed compounds and pharmaceutically acceptable salts thereof. The compounds of the present application are inhibitors of SMO in the Hh signaling pathway, and is able to inhibit or decrease the activity of SMO. In general, the compounds of the present application comprises an ester moiety (i.e., C(O)O), a thioester moiety (i.e., C(O)S), or a hydrazide moiety (i.e., C(O)NH—NH). In some embodiments, compounds of the present application comprise an ester moiety, a thioester moiety, or a hydrazide moiety in the place of an amide moiety in compounds which can inhibit or decrease the activity of SMO. For example, the compounds of the present application have the following structure:

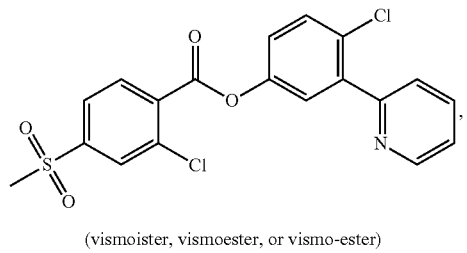

(vismoister, vismoester, or vismo-ester)

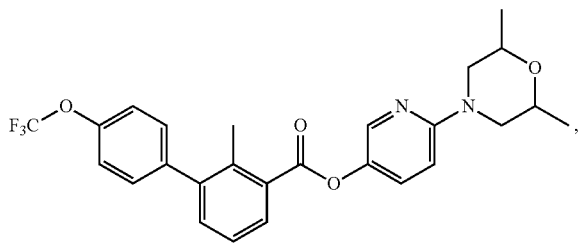

(erismoister, erismoester, or erismo-ester)

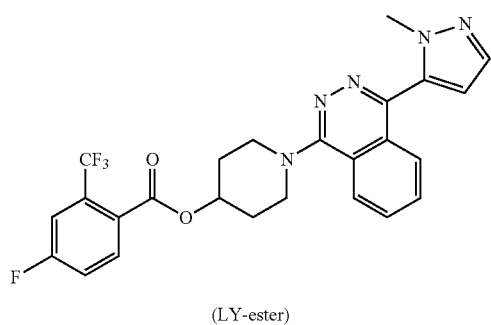

(LY-ester)

each having an ester moiety, as compared to the amide moiety in the compounds below:

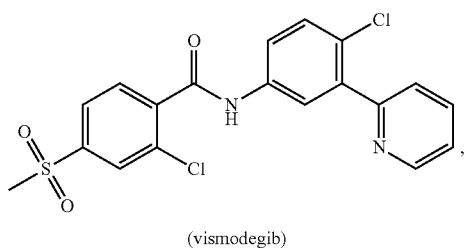

(vismodegib)

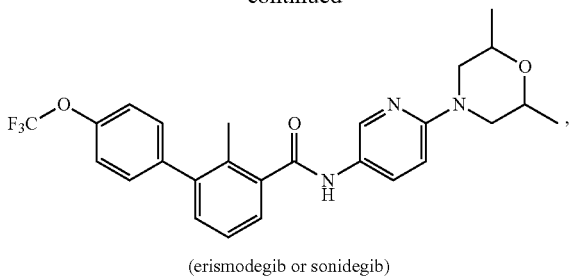

(erismodegib or sonidegib)

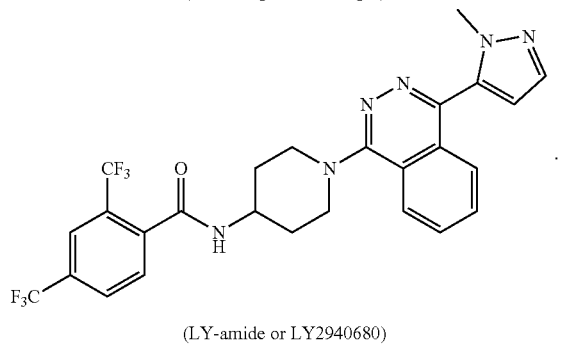

(LY-amide or LY2940680)

The compounds of the present application display various desirable properties.

In one embodiment, the compounds of the present application (e.g., vismoester, erismoester, or LY-ester) are metabolized in vivo at a rate that is at least 10%, 20%, 30%, 40%, 50%, 60%, 70%, 80%, 90%, 100%, 150%, or 200% faster than the metabolism rate of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

In one embodiment, the compounds of the present application (e.g., vismoester, erismoester, or LY-ester) can be degraded, for example, by an esterase in the serum. In one embodiment, the compounds of the present application can be degraded, for example, by a serum esterase, at a rate that is at least 10%, 20%, 30%, 40%, 50%, 60%, 70%, 80%, 90%, 100%, 150%, or 200% faster than the rate of degradation of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

In one embodiment, the compounds of the present application (e.g., vismoester, erismoester, or LY-ester) can be degraded in serum (i.e., serum from blood) with a T112 (i.e., the time when half of the compound is degraded) less than 120 hours, less than 96 hours, less than 72 hours, less than 48 hours, less than 36 hours, less than 24 hours, less than 12 hours, less than 8 hours, less than 4 hours, less than 2 hours, less than 1 hour, or less than 30 minutes.

In one embodiment, the compounds of the present application (e.g., vismoester, erismoester, or LY-ester) have a therapeutic index (TI) that is at least 1.1 fold, 1.2 fold, 1.3 fold, 1.4 fold, 1.5 fold, 2.0 fold, 2.5 fold, 3.0 fold, 3.5 fold, 4.0 fold, 4.5 fold, 5 fold, 10 fold, 15 fold, 20 fold, 30 fold, 40 fold, 50 fold, 70 fold, 100 fold, 150 fold, 200 fold, or 500 fold higher than the TI of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

In one embodiment, the compounds of the present application (e.g., vismoester, erismoester, or LY-ester) have a $LD_{50}$ that is at least 1.1 fold, 1.2 fold, 1.3 fold, 1.4 fold, 1.5 fold, 2.0 fold, 2.5 fold, 3.0 fold, 3.5 fold, 4.0 fold, 4.5 fold, 5 fold, 10 fold, 15 fold, 20 fold, 30 fold, 40 fold, 50 fold, 70 fold, 100 fold, 150 fold, 200 fold, or 500 fold higher than the $LD_{50}$ of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

In one embodiment, the compounds of the present application (e.g., vismoester, erismoester, or LY-ester) have a $TD_{50}$ that is at least 1.1 fold, 1.2 fold, 1.3 fold, 1.4 fold, 1.5 fold, 2.0 fold, 2.5 fold, 3.0 fold, 3.5 fold, 4.0 fold, 4.5 fold, 5 fold, 10 fold, 15 fold, 20 fold, 30 fold, 40 fold, 50 fold, 70 fold, 100 fold, 150 fold, 200 fold, or 500 fold higher than the $TD_{50}$ of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

In one embodiment, the compounds of the present application (e.g., vismoester, erismoester, or LY-ester) have a plasma exposure is at least 1.1 fold, 1.2 fold, 1.3 fold, 1.4 fold, 1.5 fold, 2.0 fold, 2.5 fold, 3.0 fold, 3.5 fold, 4.0 fold, 4.5 fold, 5 fold, 10 fold, 15 fold, 20 fold, 30 fold, 40 fold, 50 fold, 70 fold, 100 fold, 150 fold, 200 fold, or 500 fold less than the plasma exposure of a compound that does not have the ester moiety, the thioester moiety, or the hydrazide moiety. In one embodiment, the compound that does not have the ester moiety, the thioester moiety, or the hydrazide moiety is a compound that has an amide moiety in the place of the ester moiety, the thioester moiety, or the hydrazide moiety (e.g., vismodegib, erismodegib, or LY2040680).

The present application provides a compound of formula A:

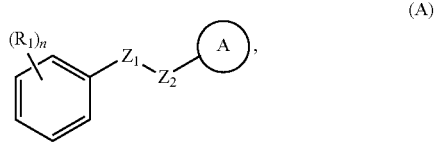

(A)

or a pharmaceutically acceptable salt thereof, wherein:
$Z_1$-$Z_2$ is C(O)—O, O—C(O), C(O)—S, S—C(O), C(O)—NR—NR, or NR—NR—C(O);
each R is independently H or $C_1$-$C_3$ alkyl;
n is 0, 1, 2, 3, 4, or 5;
each $R_1$ is independently halogen, OH, cyano, unsubstituted or substituted $C_1$-$C_6$ alkyl, unsubstituted or substituted $C_1$-$C_6$ alkoxy, C(O)-(unsubstituted or substituted $C_1$-$C_6$ alkyl), S(O)$_m$-(unsubstituted or substituted $C_1$-$C_6$ alkyl), unsubstituted or substituted phenyl, NH$_2$, NH-heteroaryl, wherein the heteroaryl comprises one or two 5- to 8-membered rings and 1-4 heteroatoms selected from O, N, and S and is optionally substituted;

m is 0, 1, or 2; and (A)

is unsubstituted or substituted phenyl, unsubstituted or substituted heteroaryl comprising one 5- or 6-membered ring and 1-3 heteroatoms selected from N, O, and S, or unsubstituted or substituted heterocyclyl comprising one 5- or 6-membered ring and 1-3 heteroatoms selected from N, O, and S.

In one embodiment, $Z_1$-$Z_2$ is C(O)—O, O—C(O), C(O)—S, or S—C(O).

In one embodiment, $Z_1$-$Z_2$ is C(O)—S, S—C(O), C(O)—NR—NR, or NR—NR—C(O).

In one embodiment, $Z_1$-$Z_2$ is C(O)—O or O—C(O).

In one embodiment, $Z_1$-$Z_2$ is C(O)—O.

In one embodiment, $Z_1$-$Z_2$ is C(O)—S or S—C(O).

In one embodiment, $Z_1$-$Z_2$ is C(O)—S.

In one embodiment, $Z_1$-$Z_2$ is C(O)—NR—NR or NR—NR—C(O).

In one embodiment, $Z_1$-$Z_2$ is C(O)—NR—NR.

In one embodiment, each R is H (i.e., $Z_1$-$Z_2$ is C(O)—NH—NH or NH—NH—C(O)).

In one embodiment, one of R is H, and the other R is $C_1$-$C_3$ alkyl (e.g., methyl, ethyl, or propyl).

In one embodiment, each R is $C_1$-$C_3$ alkyl (e.g., methyl, ethyl, or propyl).

In one embodiment, n is 0, 1, or 2.
In one embodiment, n is 0.
In one embodiment, n is 1.
In one embodiment, n is 2.
In one embodiment, n is 3.
In one embodiment, n is 4.
In one embodiment, n is 5.

In one embodiment, at least one $R_1$ is halogen (e.g., F, Cl, Br, or I).

In one embodiment, at least one $R_1$ is OH.
In one embodiment, at least one $R_1$ is cyano.
In one embodiment, at least one $R_1$ is NH$_2$.

In one embodiment, at least one $R_1$ is unsubstituted or substituted straight-chain $C_1$-$C_6$ alkyl or branched $C_3$-$C_6$ alkyl. In a further embodiment, at least one $R_1$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_1$ is unsubstituted or substituted straight-chain $C_1$-$C_6$ alkoxy or branched $C_3$-$C_6$ alkoxy. In a further embodiment, at least one $R_1$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_1$ is C(O)-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, at least one $R_1$ is S(O)$_m$-(unsubstituted or substituted $C_1$-$C_6$ alkyl). In a further embodiment, at least one $R_1$ is S-(unsubstituted or substituted $C_1$-$C_6$ alkyl). In another further embodiment, at least one $R_1$ is S(O)-(unsubstituted or substituted $C_1$-$C_6$ alkyl). In another further embodiment, at least one $R_1$ is S(O)$_2$-(unsubstituted or substituted $C_1$-$C_6$ alkyl). In a further embodiment, the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, m is 0.
In one embodiment, m is 1.
In one embodiment, m is 2.

In one embodiment, at least one $R_1$ is phenyl optionally substituted with one or more substituents independently selected from halogen, cyano, unsubstituted or substituted $C_1$-$C_6$ alkyl, unsubstituted or substituted $C_1$-$C_6$ alkoxy, S-(unsubstituted or substituted $C_1$-$C_6$ alkyl), S(O)-(unsubstituted or substituted $C_1$-$C_6$ alkyl), S(O)$_2$-(unsubstituted or substituted $C_1$-$C_6$ alkyl), amino, di-$C_1$-$C_6$ alkylamino, and unsubstituted or substituted $C_6$-$C_{10}$ aryl.

In one embodiment, at least one $R_1$ is NH-heteroaryl. In a further embodiment, the heteroaryl is selected from pyrrolyl, pyrazolyl, imidazolyl, pyridinyl, pyrimidyl, indolyl, quinolinyl, and quinazolinyl, each of which is optionally substituted with one or more substituents independently selected from halogen, OH, unsubstituted or substituted $C_1$-$C_6$ alkyl, unsubstituted or substituted $C_1$-$C_6$ alkoxy, and unsubstituted or substituted phenyl.

In one embodiment, (A)

is unsubstituted phenyl or phenyl substituted with one or more substituents independently selected from halogen, OH, cyano, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), C(O)-(unsubstituted or substituted $C_1$-$C_6$ alkoxy), C(O)NH-(unsubstituted or substituted $C_1$-$C_6$ alkyl), S-(unsubstituted or substituted $C_1$-$C_6$ alkyl), S(O)-(unsubstituted or substituted $C_1$-$C_6$ alkyl), S(O)$_2$-(unsubstituted or substituted $C_1$-$C_6$ alkyl), (CH$_2$)$_{0-6}$—NH$_2$, (CH$_2$)$_{0-6}$—NH—$C_1$-$C_6$ alkyl, (CH$_2$)$_{0-6}$—N($C_1$-$C_6$ alkyl)$_2$, unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from 0, N, and S, and unsubstituted or substituted heteroaryl comprising one or two 5- to 8-membered rings and 1-4 heteroatoms selected from O, N, and S.

In a further embodiment, (A)

is unsubstituted phenyl or phenyl substituted with one or more substituents independently selected from halogen, OH, cyano, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), C(O)-(unsubstituted or substituted $C_1$-$C_6$ alkoxy), C(O)NH-(unsubstituted or substituted $C_1$-$C_6$ alkyl), S-(unsubstituted or substituted $C_1$-$C_6$ alkyl), S(O)-(unsubstituted or substituted $C_1$-$C_6$ alkyl), S(O)$_2$-(unsubstituted or substituted $C_1$-$C_6$ alkyl), (CH$_2$)$_{0-6}$—

$NH_2$, $(CH_2)_{0-6}$—NH—$C_1$-$C_6$ alkyl, and $(CH_2)_{0-6}$—N($C_1$-$C_6$ alkyl)$_2$. In a further embodiment, (A)

is phenyl substituted with one or more substituents independently selected from halogen, OH, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), $(CH_2)_{0-6}$—$NH_2$, $(CH_2)_{0-6}$—NH—$C_1$-$C_6$ alkyl, and $(CH_2)_{0-6}$—N($C_1$-$C_6$ alkyl)$_2$.

In a further embodiment, (A)

is unsubstituted phenyl or phenyl substituted with one or more substituents independently selected from unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, and unsubstituted or substituted heteroaryl comprising one or two 5- to 8-membered rings and 1-4 heteroatoms selected from O, N, and S.

In a further embodiment, (A)

is phenyl substituted with heteroaryl selected from pyridinyl, pyrimidinyl, indolyl, imidazopyridinyl.

In one embodiment, (A)

is unsubstituted heteroaryl or heteroaryl substituted with one or more substituents independently selected from halogen, OH, cyano, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), C(O)-(unsubstituted or substituted $C_1$-$C_6$ alkoxy), C(O)NH-(unsubstituted or substituted $C_1$-$C_6$ alkyl), S-(unsubstituted or substituted $C_1$-$C_6$ alkyl), S(O)-(unsubstituted or substituted $C_1$-$C_6$ alkyl), S(O)$_2$-(unsubstituted or substituted $C_1$-$C_6$ alkyl), unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, unsubstituted or substituted heteroaryl comprising one or two 5- to 8-membered rings and 1-4 heteroatoms selected from O, N, and S, S(O)$_2$R$_2$, C(O)R$_2$, OR$_2$, and NR$_3$R$_4$, wherein:
  R$_2$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S; and R$_3$ and R$_4$ are each independently H or unsubstituted or substituted $C_1$-$C_6$ alkyl.

In a further embodiment, (A)

is heteroaryl substituted with one or more substituents independently selected from halogen, OH, cyano, unsubstituted or substituted $C_1$-$C_6$ alkyl, unsubstituted or substituted $C_1$-$C_6$ alkoxy, unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, unsubstituted or substituted heteroaryl comprising one or two 5- to 8-membered rings and 1-4 heteroatoms selected from O, N, and S, S(O)$_2$R$_2$, C(O)R$_2$, OR$_2$, and NR$_3$R$_4$.

In a further embodiment, (A)

is heteroaryl selected from pyrrolyl, pyrazolyl, imidazolyl, pyridinyl, and pyrimidinyl, each of which is optionally substituted. In a further embodiment, (A)

is optionally substituted pyridinyl.

In one embodiment, (A)

is unsubstituted heterocyclyl or heterocyclyl substituted with one or more substituents independently selected from halogen, OH, cyano, unsubstituted or substituted $C_1$-$C_6$ alkyl, unsubstituted or substituted $C_1$-$C_6$ alkoxy, unsubstituted or substituted $C_6$-$C_{10}$ aryl, and unsubstituted or substituted heteroaryl comprising one or two 5- to 8-membered rings and 1-4 heteroatoms selected from O, N, and S. In a further embodiment, (A)

is heterocyclyl substituted with one or more substituents independently selected from unsubstituted or substituted $C_6$-$C_{10}$ aryl and unsubstituted or substituted heteroaryl comprising one or two 5- to 8-membered rings and 1-4 heteroatoms selected from O, N, and S.

In a further embodiment, (A)

is heterocyclyl selected from pyrrolidinyl, piperidinyl, and piperazinyl, each of which is optionally substituted. In a further embodiment,

is optionally substituted piperidinyl.

In one embodiment, a compound of formula A is a compound of formula I:

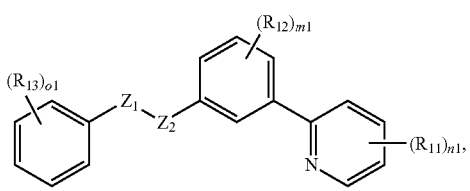

or a pharmaceutically acceptable salt thereof, wherein:

$Z_1$-$Z_2$ is C(O)—O, O—C(O), C(O)—S, S—C(O), C(O)—NR—NR, or NR—NR—C(O);

each R is independently H or $C_1$-$C_3$ alkyl;

n1 is 0, 1, 2, 3, or 4;

each $R_{11}$ is independently halogen, OH, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), C(O)-(unsubstituted or substituted $C_1$-$C_6$ alkoxy), C(O)NH-(unsubstituted or substituted $C_1$-$C_6$ alkyl), S(O)$_{p1}$-(unsubstituted or substituted $C_1$-$C_6$ alkyl), unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings s and 1-4 heteroatoms selected from O, N, and S, or unsubstituted or substituted heteroaryl comprising one or two 5- to 8-membered rings s and 1-4 heteroatoms selected from O, N, and S;

m1 is 0, 1, 2, 3, or 4;

each $R_{12}$ is independently halogen, OH, unsubstituted or substituted $C_1$-$C_6$ alkyl, unsubstituted or substituted $C_1$-$C_6$ alkoxy, or C(O)-(unsubstituted or substituted $C_1$-$C_6$ alkyl);

o1 is 0, 1, 2, 3, 4, or 5;

each $R_{13}$ is independently halogen, OH, unsubstituted or substituted $C_1$-$C_6$ alkyl, unsubstituted or substituted $C_1$-$C_6$ alkoxy, C(O)-(unsubstituted or substituted $C_1$-$C_6$ alkyl), or S(O)$_{p1}$-(unsubstituted or substituted $C_1$-$C_6$ alkyl); and p1 is 0, 1, or 2.

In one embodiment, $Z_1$-$Z_2$ is C(O)—O, O—C(O), C(O)—S, or S—C(O).

In one embodiment, $Z_1$-$Z_2$ is C(O)—S, S—C(O), C(O)—NR—NR, or NR—NR—C(O).

In one embodiment, $Z_1$-$Z_2$ is C(O)—O or O—C(O).

In one embodiment, $Z_1$-$Z_2$ is C(O)—O.

In one embodiment, $Z_1$-$Z_2$ is C(O)—S or S—C(O).

In one embodiment, $Z_1$-$Z_2$ is C(O)—S.

In one embodiment, $Z_1$-$Z_2$ is C(O)—NR—NR or NR—NR—C(O).

In one embodiment, $Z_1$-$Z_2$ is C(O)—NR—NR.

In one embodiment, each R is H (i.e., $Z_1$-$Z_2$ is C(O)—NH—NH or NH—NH—C(O)).

In one embodiment, one of R is H, and the other R is $C_1$-$C_3$ alkyl (e.g., methyl, ethyl, or propyl).

In one embodiment, each R is $C_1$-$C_3$ alkyl (e.g., methyl, ethyl, or propyl).

In one embodiment, n1 is 0, 1, or 2.

In one embodiment, n1 is 0.

In one embodiment, n1 is 1.

In one embodiment, n1 is 2.

In one embodiment, n1 is 3.

In one embodiment, n1 is 4.

In one embodiment, at least one $R_{11}$ is independently halogen, OH, unsubstituted or substituted $C_1$-$C_6$ alkyl, unsubstituted or substituted $C_1$-$C_6$ alkoxy, C(O)OH, C(O)-(unsubstituted or substituted $C_1$-$C_6$ alkyl), C(O)-(unsubstituted or substituted $C_1$-$C_6$ alkoxy), C(O)NH-(unsubstituted or substituted $C_1$-$C_6$ alkyl), or S(O)$_{p1}$-(unsubstituted or substituted $C_1$-$C_6$ alkyl).

In one embodiment, at least one $R_{11}$ is independently halogen, OH, unsubstituted or substituted $C_1$-$C_6$ alkyl, or unsubstituted or substituted $C_1$-$C_6$ alkoxy.

In one embodiment, at least one $R_{11}$ is halogen (e.g., F, Cl, Br, or I).

In one embodiment, at least one $R_{11}$ is OH.

In one embodiment, at least one $R_{11}$ is unsubstituted or substituted straight-chain $C_1$-$C_6$ alkyl or branched $C_3$-$C_6$ alkyl. In a further embodiment, at least one $R_{11}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{11}$ is unsubstituted or substituted straight-chain $C_1$-$C_6$ alkoxy or branched $C_3$-$C_6$ alkoxy. In a further embodiment, at least one $R_{11}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{11}$ is C(O)OH.

In one embodiment, at least one $R_{11}$ is C(O)-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, at least one $R_{11}$ is C(O)-(unsubstituted or substituted $C_1$-$C_6$ alkoxy), wherein the unsubstituted or substituted $C_1$-$C_6$ alkoxy is selected from methoxy, ethoxy, propoxy, i-propoxy, butoxy, i-butoxy, t-butoxy, pentoxy, and hexyloxy, each of which is optionally substituted with halogen (e.g., F, Cl, Br, or I).

In one embodiment, at least one $R_{11}$ is C(O)NH-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, at least one $R_{11}$ is S(O)$_{p1}$-(unsubstituted or substituted $C_1$-$C_6$ alkyl). In a further embodiment, at least one $R_{11}$ is S-(unsubstituted or substituted $C_1$-$C_6$ alkyl). In another further embodiment, at least one $R_{11}$ is S(O)-(unsubstituted or substituted $C_1$-$C_6$ alkyl). In another further embodiment, at least one $R_{11}$ is S(O)$_2$-(unsubstituted or substituted $C_1$-$C_6$ alkyl). In a further embodiment, the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, at least one $R_{11}$ is $C_3$-$C_8$ cycloalkyl selected from cyclopropyl, cyclobutyl, cyclopentyl, cyclohexyl, cycloheptyl, and cyclooctyl, each of which is optionally substituted with one or more substituents independently selected from halogen, OH, cyano, nitro, $C_1$-$C_6$ alkyl, $C_1$-$C_6$ alkoxy, and amino.

In one embodiment, at least one $R_{11}$ is phenyl optionally substituted with one or more substituents independently selected from halogen, OH, cyano, nitro, $C_1$-$C_6$ alkyl, $C_1$-$C_6$ alkoxy, and amino.

In one embodiment, at least one $R_{11}$ is heterocyclyl optionally substituted with one or more substituents independently selected from halogen, OH, cyano, nitro, $C_1$-$C_6$ alkyl, $C_1$-$C_6$ alkoxy, and amino. In a further embodiment, at least one $R_{11}$ is heterocyclyl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, at least one $R_{11}$ is heteroaryl optionally substituted with one or more substituents independently selected from halogen, OH, cyano, nitro, $C_1$-$C_6$ alkyl, $C_1$-$C_6$ alkoxy, and amino. In a further embodiment, at least one $R_{11}$ is heteroaryl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, m1 is 0, 1, or 2.
In one embodiment, m1 is 0.
In one embodiment, m1 is 1.
In one embodiment, m1 is 2.
In one embodiment, m1 is 3.
In one embodiment, m1 is 4.

In one embodiment, at least one $R_{12}$ is halogen (e.g., F, Cl, Br, or I). In a further embodiment, at least one $R_{12}$ is $C_1$.

In one embodiment, at least one $R_{12}$ is OH.

In one embodiment, at least one $R_{12}$ is unsubstituted or substituted straight-chain $C_1$-$C_6$ alkyl or branched $C_3$-$C_6$ alkyl. In a further embodiment, at least one $R_{12}$ is methyl, ethyl, propyl, i-propyl, butyl, i-butyl, t-butyl, pentyl, or hexyl, each of which is optionally substituted with halogen (e.g., F, Cl, Br, or I), amino, nitro, $C_1$-$C_6$ alkylsulfonyl, or $C_1$-$C_6$ alkoxy.

In one embodiment, at least one $R_{12}$ is unsubstituted or substituted straight-chain $C_1$-$C_6$ alkoxy or branched $C_3$-$C_6$ alkoxy. In a further embodiment, at least one $R_{12}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{12}$ is C(O)-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I), amino, nitro, $C_1$-$C_6$ alkylsulfonyl, or $C_1$-$C_6$ alkoxy.

In one embodiment, o1 is 0, 1, or 2.
In one embodiment, o1 is 0.
In one embodiment, o1 is 1.
In one embodiment, o1 is 2.
In one embodiment, o1 is 3.
In one embodiment, o1 is 4.
In one embodiment, o1 is 5.

In one embodiment, at least one $R_{13}$ is halogen (e.g., F, Cl, Br, or I). In a further embodiment, at least one $R_{13}$ is $C_1$.

In one embodiment, at least one $R_{13}$ is OH.

In one embodiment, at least one $R_{13}$ is unsubstituted or substituted straight-chain $C_1$-$C_6$ alkyl or branched $C_3$-$C_6$ alkyl. In a further embodiment, at least one $R_{13}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{13}$ is unsubstituted or substituted straight-chain $C_1$-$C_6$ alkoxy or branched $C_3$-$C_6$ alkoxy. In a further embodiment, at least one $R_{13}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{13}$ is C(O)-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, at least one $R_{13}$ is $S(O)_{p1}$-(unsubstituted or substituted $C_1$-$C_6$ alkyl). In a further embodiment, at least one $R_{13}$ is S-(unsubstituted or substituted $C_1$-$C_6$ alkyl). In another further embodiment, at least one $R_{13}$ is S(O)-(unsubstituted or substituted $C_1$-$C_6$ alkyl). In another further embodiment, at least one $R_{13}$ is $S(O)_2$-(unsubstituted or substituted $C_1$-$C_6$ alkyl). In a further embodiment, the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I). In a further embodiment, at least one $R_{13}$ is $S(O)_2$—$CH_3$.

In one embodiment, p1 is 0.
In one embodiment, p1 is 1.
In one embodiment, p1 is 2.

Any of the groups described above for any of $Z_1$, $Z_2$, R, $R_{11}$, $R_{12}$, $R_{13}$, n1, m1, o1, and p1 can be combined with any of the groups described above for one or more of the remainder of $Z_1$, $Z_2$, R, $R_{11}$, $R_{12}$, $R_{13}$, n1, m1, o1, and p1.

In one embodiment, $Z_1$-$Z_2$ is C(O)—O or O—C(O); n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, $Z_1$-$Z_2$ is C(O)—O; n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, $Z_1$-$Z_2$ is C(O)—S or S—C(O); n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, $Z_1$-$Z_2$ is C(O)—S; n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, $Z_1$-$Z_2$ is C(O)—NH—NH or NH—NH—C(O); n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, $Z_1$-$Z_2$ is C(O)—NH—NH; n1 is 0; m1 is 0 or 1; $R_{12}$ is halogen (e.g., F, Cl, Br, or I); o1 is 0, 1, or 2; and $R_{13}$ is halogen (e.g., F, Cl, Br, or I), unsubstituted or substituted straight-chain $C_1$-$C_6$ alkyl or branched $C_3$-$C_6$ alkyl, or $S(O)_{p1}$-(unsubstituted or substituted $C_1$-$C_6$ alkyl). In a further embodiment, $R_{12}$ is F or Cl; and $R_{13}$ is F, Cl, methyl, ethyl, propyl, or $S(O)_2$-(unsubstituted or substituted $C_1$-$C_6$ alkyl). In a further embodiment, $R_{12}$ is $C_1$; o1 is 2; and $R_{13}$ is Cl or $S(O)_2$—$CH_3$.

In one embodiment, a compound of formula I is a compound of formula Ia:

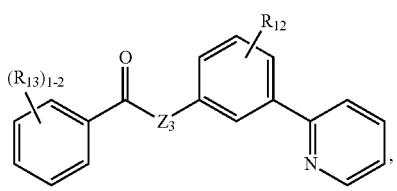

(Ia)

or a pharmaceutically acceptable salt thereof, wherein $Z_3$ is O, S, or NR—NR; and R, $R_{12}$, $R_{13}$, and p1 are each as defined above in formula I.

In one embodiment, $Z_3$ is O.

In one embodiment, $Z_3$ is S.

In one embodiment, $Z_3$ is NR.

In one embodiment, $R_{12}$ is halogen. In a further embodiment, $R_{12}$ is F or Cl. In a further embodiment, $R_{12}$ is $C_1$.

In one embodiment, at least one $R_{13}$ is halogen. In a further embodiment, at least one $R_{13}$ is F or Cl. In a further embodiment, at least one $R_{13}$ is $C_1$.

In one embodiment, at least one $R_{13}$ is $S(O)_2$-(unsubstituted or substituted $C_1$-$C_6$ alkyl), wherein the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I). In a further embodiment, at least one $R_{13}$ is $S(O)_2$—$CH_3$.

In one embodiment, one $R_{13}$ is halogen, and the other $R_{13}$ is $S(O)_2$-(unsubstituted or substituted $C_1$-$C_6$ alkyl), wherein the unsubstituted or substituted $C_1$-$C_6$ alkyl is selected from methyl, ethyl, propyl. In a further embodiment, one $R_{13}$ is Cl, and the other $R_{13}$ is $S(O)_2$—$CH_3$.

Any of $Z_3$, R, $R_{12}$ and $R_{13}$, and p1 can be selected from any of the groups described above and combined with any of the groups described above for one or more of the remainder of $Z_3$, R, $R_{12}$ and $R_{13}$, and p1.

In one embodiment, a compound of formula A is a compound of formula II:

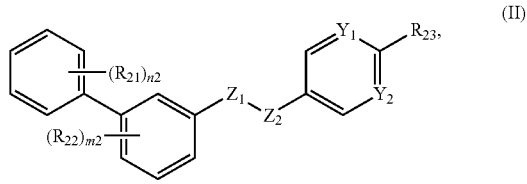

(II)

or a pharmaceutically acceptable salt thereof, wherein:
$Z_1$-$Z_2$ is C(O)—O, O—C(O), C(O)—S, S—C(O), C(O)—NR—NR, or NR—NR—C(O);
each R is independently H or $C_1$-$C_3$ alkyl;
$Y_1$ and $Y_2$ are each independently N or $CR_{24}$;
each $R_{24}$ is independently H, halogen, cyano, unsubstituted or substituted $C_1$-$C_6$ alkyl, or unsubstituted or substituted $C_1$-$C_6$ alkoxy;
n2 is 0, 1, 2, 3, 4, or 5;
each $R_{21}$ is independently halogen, cyano, unsubstituted or substituted $C_1$-$C_6$ alkyl, unsubstituted or substituted $C_1$-$C_6$ alkoxy, $S(O)_{o2}$-(unsubstituted or substituted $C_1$-$C_6$ alkyl), amino, di-$C_1$-$C_6$ alkylamino, or unsubstituted or substituted $C_6$-$C_{10}$ aryl;
o2 is 0, 1, or 2;
m2 is 0, 1, 2, 3, or 4;
each $R_{22}$ is independently halogen, unsubstituted or substituted $C_1$-$C_6$ alkyl, or unsubstituted or substituted $C_1$-$C_6$ alkoxy;
$R_{23}$ is $R_{25}$, $S(O)_2R_{25}$, $C(O)R_{25}$, $OR_{25}$, or $NR_{26}R_{27}$;
$R_{25}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S; and
$R_{26}$ and $R_{27}$ are each independently H or unsubstituted or substituted $C_1$-$C_6$ alkyl.

In one embodiment, $Z_1$-$Z_2$ is C(O)—O, O—C(O), C(O)—S, or S—C(O).

In one embodiment, $Z_1$-$Z_2$ is C(O)—S, S—C(O), C(O)—NR—NR, or NR—NR—C(O).

In one embodiment, $Z_1$-$Z_2$ is C(O)—O or O—C(O).

In one embodiment, $Z_1$-$Z_2$ is C(O)—O.

In one embodiment, $Z_1$-$Z_2$ is C(O)—S or S—C(O).

In one embodiment, $Z_1$-$Z_2$ is C(O)—S.

In one embodiment, $Z_1$-$Z_2$ is C(O)—NR—NR or NR—NR—C(O).

In one embodiment, $Z_1$-$Z_2$ is C(O)—NR—NR.

In one embodiment, each R is H (i.e., $Z_1$-$Z_2$ is C(O)—NH—NH or NH—NH—C(O)).

In one embodiment, one of R is H, and the other R is $C_1$-$C_3$ alkyl (e.g., methyl, ethyl, or propyl).

In one embodiment, each R is $C_1$-$C_3$ alkyl (e.g., methyl, ethyl, or propyl).

In one embodiment, $Y_1$ is N and $Y_2$ is N.

In one embodiment, $Y_1$ is N and $Y_2$ is $CR_{24}$. In a further embodiment, $R_{24}$ is H. In another further embodiment, $R_{24}$ is halogen (e.g., F, Cl, Br, or I), cyano, unsubstituted or substituted $C_1$-$C_6$ alkyl (e.g., methyl, ethyl, propyl, i-propyl, butyl, i-butyl, t-butyl, pentyl, or hexyl, each of which is optionally substituted with halogen (e.g., F, Cl, Br, or I)), or unsubstituted or substituted $C_1$-$C_6$ alkoxy (e.g., methoxy, ethoxy, propoxy, i-propoxy, butoxy, i-butoxy, t-butoxy, pentoxy, or hexyloxy, each of which is optionally substituted with halogen (e.g., F, Cl, Br, or I)).

In one embodiment, $Y_1$ is $CR_{24}$ and $Y_2$ is $CR_{24}$. In a further embodiment, each $R_{24}$ is H. In another further embodiment, one $R_{24}$ is H, and the other $R_{24}$ is halogen (e.g., F, Cl, Br, or I), cyano, unsubstituted or substituted $C_1$-$C_6$ alkyl (e.g., methyl, ethyl, propyl, i-propyl, butyl, i-butyl, t-butyl, pentyl, or hexyl, each of which is optionally substituted with halogen (e.g., F, Cl, Br, or I)), or unsubstituted or substituted $C_1$-$C_6$ alkoxy (e.g., methoxy, ethoxy, propoxy, i-propoxy, butoxy, i-butoxy, t-butoxy, pentoxy, or hexyloxy, each of which is optionally substituted with halogen (e.g., F, Cl, Br, or I)). In another further embodiment, each $R_{24}$ is independently halogen (e.g., F, Cl, Br, or I), cyano, unsubstituted or substituted $C_1$-$C_6$ alkyl (e.g., methyl, ethyl, propyl, i-propyl, butyl, i-butyl, t-butyl, pentyl, or hexyl, each of which is optionally substituted with halogen (e.g., F, Cl, Br, or I)), or unsubstituted or substituted $C_1$-$C_6$ alkoxy (e.g., methoxy, ethoxy, propoxy, i-propoxy, butoxy, i-butoxy, t-butoxy, pentoxy, or hexyloxy, each of which is optionally substituted with halogen (e.g., F, Cl, Br, or I)).

In one embodiment, n2 is 0, 1, or 2.
In one embodiment, n2 is 0.
In one embodiment, n2 is 1.
In one embodiment, n2 is 2.
In one embodiment, n2 is 3.
In one embodiment, n2 is 4.
In one embodiment, n2 is 5.

In one embodiment, at least one $R_{21}$ is halogen (e.g., F, Cl, Br, or I).

In one embodiment, at least one $R_{21}$ is cyano.

In one embodiment, at least one $R_{21}$ is unsubstituted or substituted straight-chain $C_1$-$C_6$ alkyl or branched $C_3$-$C_6$ alkyl. In a further embodiment, $R_{21}$ is methyl, ethyl, propyl, propyl, butyl, i-butyl, t-butyl, pentyl, or hexyl, each of which is optionally substituted with halogen (e.g., F, Cl, Br, or I).

In one embodiment, at least one $R_{21}$ is unsubstituted or substituted straight-chain $C_1$-$C_6$ alkoxy or branched $C_3$-$C_6$ alkoxy. In a further embodiment, at least one $R_{21}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I). In a further embodiment, at least one $R_{21}$ is trifluoromethoxy.

In one embodiment, at least one $R_{21}$ is $S(O)_{o2}$-(unsubstituted or substituted $C_1$-$C_6$ alkyl). In a further embodiment, at least one $R_{21}$ is S-(unsubstituted or substituted $C_1$-$C_6$ alkyl). In another further embodiment, at least one $R_{21}$ is S(O)-(unsubstituted or substituted $C_1$-$C_6$ alkyl). In another further embodiment, at least one $R_{21}$ is $S(O)_2$-(unsubstituted or substituted $C_1$-$C_6$ alkyl). In a further embodiment, the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, o2 is 0.
In one embodiment, o2 is 1.
In one embodiment, o2 is 2.

In one embodiment, at least one $R_{21}$ is dimethylamino, diethylamino, or dipropylamino.

In one embodiment, at least one $R_{21}$ is phenyl optionally substituted with one or more substituents independently selected from halogen, OH, cyano, nitro, $C_1$-$C_6$ alkyl, $C_1$-$C_6$ alkoxy, and amino.

In one embodiment, m2 is 0, 1, or 2.
In one embodiment, m2 is 0.
In one embodiment, m2 is 1.
In one embodiment, m2 is 2.
In one embodiment, m2 is 3.
In one embodiment, m2 is 4.

In one embodiment, at least one $R_{22}$ is halogen (e.g., F, Cl, Br, or I).

In one embodiment, at least one $R_{22}$ is unsubstituted or substituted straight-chain $C_1$-$C_6$ alkyl or branched $C_3$-$C_6$ alkyl. In a further embodiment, at least one $R_{22}$ is methyl, ethyl, propyl, i-propyl, butyl, i-butyl, t-butyl, pentyl, or hexyl, each of which is optionally substituted with halogen (e.g., F, Cl, Br, or I). In one embodiment, at least one $R_{22}$ is methyl.

In one embodiment, at least one $R_{22}$ is unsubstituted or substituted straight-chain $C_1$-$C_6$ alkoxy or branched $C_3$-$C_6$ alkoxy. In a further embodiment, at least one $R_{22}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, $R_{23}$ is $C_3$-$C_8$ cycloalkyl selected from cyclopropyl, cyclobutyl, cyclopentyl, cyclohexyl, cycloheptyl, and cyclooctyl, each of which is optionally substituted with one or more substituents independently selected from halogen, OH, cyano, nitro, $C_1$-$C_6$ alkyl, $C_1$-$C_6$ alkoxy, and amino.

In one embodiment, $R_{23}$ is phenyl optionally substituted with one or more substituents independently selected from halogen, OH, cyano, nitro, $C_1$-$C_6$ alkyl, $C_1$-$C_6$ alkoxy, and amino.

In one embodiment, $R_{23}$ is heterocyclyl optionally substituted with one or more substituents independently selected from halogen, OH, cyano, nitro, $C_1$-$C_6$ alkyl, $C_1$-$C_6$ alkoxy, and amino. In a further embodiment, $R_{23}$ is heterocyclyl comprising a 5- or 6-membered ring optionally substituted with one or more substituents independently selected from halogen, OH, cyano, nitro, $C_1$-$C_6$ alkyl, $C_1$-$C_6$ alkoxy, and amino. In a further embodiment, $R_{23}$ is heterocyclyl selected from piperidinyl, piperazinyl, or morpholinyl, each of which is optionally substituted with one or more substituents independently selected from halogen, OH, cyano, nitro, $C_1$-$C_6$ alkyl, $C_1$-$C_6$ alkoxy, and amino. In a further embodiment, $R_{23}$ is morpholinyl optionally substituted with one or more substituents independently selected from halogen, OH, cyano, nitro, $C_1$-$C_6$ alkyl, $C_1$-$C_6$ alkoxy, and amino. In a further embodiment, $R_{23}$ is morpholinyl substituted with two substituents independently selected from methyl, ethyl, or propyl.

In one embodiment, $R_{23}$ is heteroaryl optionally substituted with one or more substituents independently selected from halogen, OH, cyano, nitro, $C_1$-$C_6$ alkyl, $C_1$-$C_6$ alkoxy, and amino. In a further embodiment, $R_{23}$ is heteroaryl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, $R_{23}$ is $S(O)_2R_{25}$ or $C(O)R_{25}$.
In one embodiment, $R_{23}$ is $OR_{25}$ or $NR_{26}R_{27}$.
In one embodiment, $R_{23}$ is $S(O)_2R_{25}$.
In one embodiment, $R_{23}$ is $C(O)R_{25}$.
In one embodiment, $R_{23}$ is $OR_{25}$.
In one embodiment, $R_{23}$ is $NR_{26}R_{27}$.

In one embodiment, $R_{25}$ is $C_3$-$C_8$ cycloalkyl selected from cyclopropyl, cyclobutyl, cyclopentyl, cyclohexyl, cycloheptyl, and cyclooctyl, each of which is optionally substituted with one or more substituents independently selected from halogen, OH, cyano, nitro, $C_1$-$C_6$ alkyl, $C_1$-$C_6$ alkoxy, and amino.

In one embodiment, $R_{25}$ is phenyl optionally substituted with one or more substituents independently selected from halogen, OH, cyano, nitro, $C_1$-$C_6$ alkyl, $C_1$-$C_6$ alkoxy, and amino.

In one embodiment, $R_{25}$ is heterocyclyl optionally substituted with one or more substituents independently selected from halogen, OH, cyano, nitro, $C_1$-$C_6$ alkyl, $C_1$-$C_6$ alkoxy, and amino. In a further embodiment, $R_{25}$ is heterocyclyl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, $R_{25}$ is heteroaryl optionally substituted with one or more substituents independently selected from halogen, OH, cyano, nitro, $C_1$-$C_6$ alkyl, $C_1$-$C_6$ alkoxy, and amino. In a further embodiment, $R_{25}$ is heteroaryl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, $R_{26}$ and $R_{27}$ are each H.

In one embodiment, one of $R_{26}$ and $R_{27}$ is H, and the other is unsubstituted or substituted straight-chain $C_1$-$C_6$ alkyl or branched $C_3$-$C_6$ alkyl. In a further embodiment, one of $R_{26}$ and $R_{27}$ is H, and the other is methyl, ethyl, propyl, i-propyl, butyl, i-butyl, t-butyl, pentyl, or hexyl, each of which is optionally substituted with halogen (e.g., F, Cl, Br, or I).

In one embodiment, $R_{26}$ and $R_{27}$ are each independently unsubstituted or substituted straight-chain $C_1$-$C_6$ alkyl or branched $C_3$-$C_6$ alkyl. In a further embodiment, $R_{26}$ and $R_{27}$ are each independently methyl, ethyl, propyl, i-propyl, butyl, i-butyl, t-butyl, pentyl, or hexyl, each of which is optionally substituted with halogen (e.g., F, Cl, Br, or I).

Any of the groups described above for any of $Z_1$, $Z_2$, $Y_1$, $Y_2$, R, $R_{21}$, $R_{22}$, $R_{23}$, $R_{24}$, $R_{25}$, $R_{26}$, $R_{27}$, n2, m2, and o2 can be combined with any of the groups described above for one or more of the remainder of $Z_1$, $Z_2$, $Y_1$, $Y_2$, R, $R_{21}$, $R_{22}$, $R_{23}$, $R_{24}$, $R_{25}$, $R_{26}$, $R_{27}$, n2, m2, and o2.

In one embodiment, $Z_1$-$Z_2$ is C(O)—O or O—C(O); $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from O, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, $Z_1$-$Z_2$ is C(O)—O; $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from O, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, $Z_1$-$Z_2$ is C(O)—S or S—C(O); $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from O, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, $Z_1$-$Z_2$ is C(O)—S; $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from O, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, $Z_1$-$Z_2$ is C(O)—NH—NH or NH—NH—C(O); $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from 0, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, $Z_1$-$Z_2$ is C(O)—NH—NH; $Y_1$ is N and $Y_2$ is $CR_{24}$; n2 is 0 or 1; m2 is 0 or 1; $R_{21}$ is unsubstituted or substituted $C_1$-$C_6$ alkyl or unsubstituted or substituted $C_1$-$C_6$ alkoxy; $R_{22}$ is unsubstituted or substituted $C_1$-$C_6$ alkyl or unsubstituted or substituted $C_1$-$C_6$ alkoxy. In a further embodiment, $R_{24}$ is H. In a further embodiment, $R_{23}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{23}$ is unsubstituted or substituted $C_3$-$C_8$ cycloalkyl or unsubstituted or substituted heterocyclyl comprising one or two 5- to 8-membered rings and 1-4 heteroatoms selected from O, N, and S. In a further embodiment, $R_{23}$ is unsubstituted or substituted heterocyclyl comprising one or two 5- to 8-membered rings and 1-4 heteroatoms selected from O, N, and S. In a further embodiment, $R_{23}$ is unsubstituted or substituted morpholinyl.

In one embodiment, a compound of formula II is a compound of formula IIa:

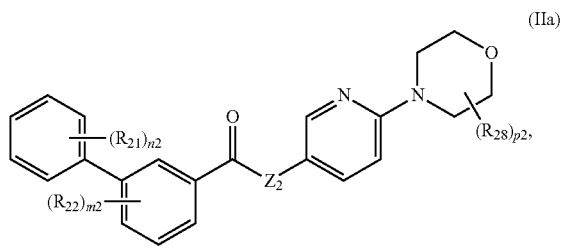

or a pharmaceutically acceptable salt thereof, wherein:
$Z_3$ is O, S, or NR—NR;
p2 is 0, 1, 2, 3, or 4;
each $R_{28}$ is independently unsubstituted or substituted $C_1$-$C_6$ alkyl; and
R, $R_{21}$, $R_{22}$, n2, m2, and o2 are each as defined above in formula II.
In one embodiment, $Z_3$ is O.
In one embodiment, $Z_3$ is S.
In one embodiment, $Z_3$ is NR.
In one embodiment, p2 is 0, 1, or 2.
In one embodiment, p2 is 0.
In one embodiment, p2 is 1.
In one embodiment, p2 is 2.
In one embodiment, p2 is 3.
In one embodiment, p2 is 4.
In one embodiment, each $R_{28}$ is independently unsubstituted or substituted straight-chain $C_1$-$C_6$ alkyl or branched $C_3$-$C_6$ alkyl. In a further embodiment, at least one $R_{11}$ is methyl, ethyl, propyl, i-propyl, butyl, i-butyl, t-butyl, pentyl, or hexyl, each of which is optionally substituted with halogen (e.g., F, Cl, Br, or I). In one embodiment, each $R_{28}$ is independently methyl, ethyl, or propyl. In one embodiment, each $R_{28}$ is methyl.
In one embodiment, n2 is 1.
In one embodiment, at least one $R_{21}$ is at the para-position of the phenyl. In one embodiment, at least one $R_{21}$ is unsubstituted or substituted straight-chain $C_1$-$C_6$ alkoxy or branched $C_3$-$C_6$ alkoxy. In a further embodiment, at least one $R_{21}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I). In a further embodiment, at least one $R_{21}$ is trifluoromethoxy.

In one embodiment, m2 is 1.

In one embodiment, at least one $R_{22}$ is unsubstituted or substituted straight-chain $C_1$-$C_6$ alkyl or branched $C_3$-$C_6$ alkyl. In a further embodiment, at least one $R_{22}$ is methyl, ethyl, propyl, i-propyl, butyl, i-butyl, t-butyl, pentyl, or hexyl, each of which is optionally substituted with halogen (e.g., F, Cl, Br, or I). In one embodiment, at least one $R_{22}$ is methyl.

Any of $Z_3$, R, $R_{21}$, $R_{22}$, $R_{28}$, n2, m2, o2, and p2 can be selected from any of the groups described above and combined with any of the groups described above for one or more of the remainder of $Z_3$, R, $R_{21}$, $R_{22}$, $R_{28}$, n2, m2, o2, and p2.

In one embodiment, a compound of formula A is a compound of formula III:

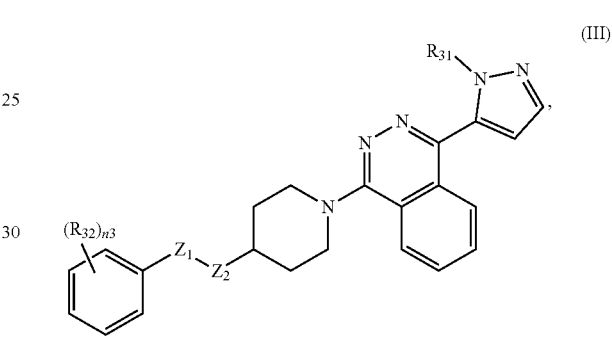

or a pharmaceutically acceptable salt thereof, wherein:
$Z_1$-$Z_2$ is C(O)—O, O—C(O), C(O)—S, S—C(O), C(O)—NR—NR, or NR—NR—C(O);
each R is independently H or $C_1$-$C_3$ alkyl;
$R_{31}$ is H or unsubstituted or substituted $C_1$-$C_6$ alkyl;
n3 is 0, 1, 2, 3, 4, or 5;
each $R_{32}$ is independently halogen, cyano, unsubstituted or substituted $C_1$-$C_6$ alkyl, unsubstituted or substituted $C_1$-$C_6$ alkoxy, or S(O)$_m$3-(unsubstituted or substituted $C_1$-$C_6$ alkyl); and
m3 is 0, 1, or 2.
In one embodiment, $Z_1$-$Z_2$ is C(O)—O, O—C(O), C(O)—S, or S—C(O).
In one embodiment, $Z_1$-$Z_2$ is C(O)—S, S—C(O), C(O)—NR—NR, or NR—NR—C(O).
In one embodiment, $Z_1$-$Z_2$ is C(O)—O or O—C(O).
In one embodiment, $Z_1$-$Z_2$ is C(O)—O.
In one embodiment, $Z_1$-$Z_2$ is C(O)—S or S—C(O).
In one embodiment, $Z_1$-$Z_2$ is C(O)—S.
In one embodiment, $Z_1$-$Z_2$ is C(O)—NR—NR or NR—NR—C(O).
In one embodiment, $Z_1$-$Z_2$ is C(O)—NR—NR.
In one embodiment, each R is H (i.e., $Z_1$-$Z_2$ is C(O)—NH—NH or NH—NH—C(O)).
In one embodiment, one of R is H, and the other R is $C_1$-$C_3$ alkyl (e.g., methyl, ethyl, or propyl).
In one embodiment, each R is $C_1$-$C_3$ alkyl (e.g., methyl, ethyl, or propyl).
In one embodiment, $R_{31}$ is H.
In one embodiment, $R_{31}$ is unsubstituted or substituted straight-chain $C_1$-$C_6$ alkyl or branched $C_3$-$C_6$ alkyl. In a further embodiment, $R_{31}$ is methyl, ethyl, propyl, i-propyl, butyl, i-butyl, t-butyl, pentyl, or hexyl, each of which is optionally substituted with halogen (e.g., F, Cl, Br, or I). In a further embodiment, $R_{31}$ is methyl, ethyl, or propyl. In a further embodiment, $R_{31}$ is methyl.

In one embodiment, n3 is 0, 1, or 2.
In one embodiment, n3 is 0.
In one embodiment, n3 is 1.
In one embodiment, n3 is 2.
In one embodiment, n3 is 3.
In one embodiment, n3 is 4.
In one embodiment, n3 is 5.
In one embodiment, at least one $R_{32}$ is halogen (e.g., F, Cl, Br, or I).

In one embodiment, at least one $R_{32}$ is cyano.

In one embodiment, at least one $R_{32}$ is unsubstituted or substituted straight-chain $C_1$-$C_6$ alkyl or branched $C_3$-$C_6$ alkyl. In a further embodiment, at least one $R_{32}$ is methyl, ethyl, propyl, i-propyl, butyl, i-butyl, t-butyl, pentyl, or hexyl, each of which is optionally substituted with halogen (e.g., F, Cl, Br, or I). In a further embodiment, at least one $R_{32}$ is methyl, ethyl, or propyl. In a further embodiment, at least one $R_{32}$ is methyl optionally substituted with one or more halogen (e.g., F, Cl, Br, or I). In a further embodiment, at least one $R_{32}$ is methyl substituted with one or more F. In a further embodiment, at least one $R_{32}$ is $CF_3$.

In one embodiment, at least one $R_{32}$ is unsubstituted or substituted straight-chain $C_1$-$C_6$ alkoxy or branched $C_3$-$C_6$ alkoxy. In a further embodiment, at least one $R_{32}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{32}$ is $S(O)_{m3}$-(unsubstituted or substituted $C_1$-$C_6$ alkyl). In a further embodiment, at least one $R_{32}$ is S-(unsubstituted or substituted $C_1$-$C_6$ alkyl). In another further embodiment, at least one $R_{32}$ is S(O)-(unsubstituted or substituted $C_1$-$C_6$ alkyl). In another further embodiment, at least one $R_{32}$ is $S(O)_2$-(unsubstituted or substituted $C_1$-$C_6$ alkyl). In a further embodiment, the unsubstituted or substituted $C_1$-$C_6$ alkyl is selected from methyl, ethyl, propyl, i-propyl, butyl, i-butyl, t-butyl, pentyl, and hexyl, each of which is optionally substituted with halogen (e.g., F, Cl, Br, or I).

In one embodiment, m3 is 0.
In one embodiment, m3 is 1.
In one embodiment, m3 is 2.

Any of the groups described above for any of $Z_1$, $Z_2$, R, $R_{31}$, $R_{32}$, n3, and m3 can be combined with any of the groups described above for one or more of the remainder of $Z_1$, $Z_2$, R, $R_{31}$, $R_{32}$, n3, and m3.

In one embodiment, $Z_1$-$Z_2$ is C(O)—O or O—C(O); $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, $Z_1$-$Z_2$ is C(O)—O; $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, $Z_1$-$Z_2$ is C(O)—S or S—C(O); $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, $Z_1$-$Z_2$ is C(O)—S; $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, $Z_1$-$Z_2$ is C(O)—NH—NH or NH—NH—C(O); $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, $Z_1$-$Z_2$ is C(O)—NH—NH; $R_{31}$ is unsubstituted or substituted straight-chain $C_1$-$C_6$ alkyl or branched $C_3$-$C_6$ alkyl; and n3 is 1 or 2. In a further embodiment, n3 is 2; one $R_{32}$ is halogen (e.g., F, Cl, Br, or I) and the other $R_{32}$ is unsubstituted or substituted straight-chain $C_1$-$C_6$ alkyl or branched $C_3$-$C_6$ alkyl. In a further embodiment, one $R_{32}$ is halogen (e.g., F, Cl, Br, or I) and the other $R_{32}$ is methyl optionally substituted with one or more halogen (e.g., F, Cl, Br, or I). In a further embodiment, one $R_{32}$ is F and the other $R_{32}$ is $CF_3$.

In one embodiment, a compound of formula III is a compound of formula IIIa:

(IIIa)

or a pharmaceutically acceptable salt thereof, wherein $Z_3$ is O, S, or NR—NR; and R, $R_{32}$, n3, and m3 are each as defined above in formula III.

In one embodiment, $Z_3$ is O.
In one embodiment, $Z_3$ is S.
In one embodiment, $Z_3$ is NR.
In one embodiment, n3 is 2.

Any of $Z_3$, R, $R_{32}$, n3, and m3 can be selected from any of the groups described above and combined with any of the groups described above for one or more of the remainder of $Z_3$, R, $R_{32}$, n3, and m3.

In one embodiment, a compound of formula A is a compound of formula IV:

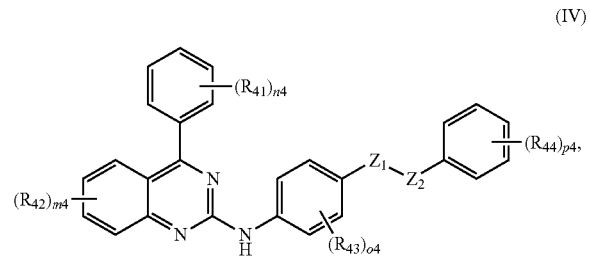

or a pharmaceutically acceptable salt thereof, wherein:
$Z_1$-$Z_2$ is C(O)—O, O—C(O), C(O)—S, S—C(O), C(O)—NR—NR, or NR—NR—C(O);
each R is independently H or $C_1$-$C_3$ alkyl;
n4 and p4 are each independently 0, 1, 2, 3, 4, or 5;
m4 and o4 are each independently 0, 1, 2, 3, or 4;
each $R_{41}$, each $R_{42}$, and each $R_{43}$ are independently halogen, OH, unsubstituted or substituted $C_1$-$C_6$ alkyl, or unsubstituted or substituted $C_1$-$C_6$ alkoxy;
each $R_{44}$ is independently halogen, OH, unsubstituted or substituted $C_1$-$C_6$ alkyl, unsubstituted or substituted $C_1$-$C_6$ alkoxy, $(CH_2)_{q4}$—$NH_2$, $(CH_2)_{q4}$—NH—$C_1$-$C_6$ alkyl, or $(CH_2)_{q4}$—N($C_1$-$C_6$ alkyl)$_2$; and
$q_4$ is 0, 1, 2, 3, 4, 5, or 6.

In one embodiment, $Z_1$-$Z_2$ is C(O)—O, O—C(O), C(O)—S, or S—C(O).

In one embodiment, $Z_1$-$Z_2$ is C(O)—S, S—C(O), C(O)—NR—NR, or NR—NR—C(O).

In one embodiment, $Z_1$-$Z_2$ is C(O)—O or O—C(O).
In one embodiment, $Z_1$-$Z_2$ is C(O)—O.
In one embodiment, $Z_1$-$Z_2$ is C(O)—S or S—C(O).
In one embodiment, $Z_1$-$Z_2$ is C(O)—S.
In one embodiment, $Z_1$-$Z_2$ is C(O)—NR—NR or NR—NR—C(O).
In one embodiment, $Z_1$-$Z_2$ is C(O)—NR—NR.
In one embodiment, each R is H (i.e., $Z_1$-$Z_2$ is C(O)—NH—NH or NH—NH—C(O)).
In one embodiment, one of R is H, and the other R is $C_1$-$C_3$ alkyl (e.g., methyl, ethyl, or propyl).
In one embodiment, each R is $C_1$-$C_3$ alkyl (e.g., methyl, ethyl, or propyl).
In one embodiment, n4 is 0, 1, or 2.
In one embodiment, n4 is 0.
In one embodiment, n4 is 1.
In one embodiment, n4 is 2.
In one embodiment, n4 is 3.
In one embodiment, n4 is 4.
In one embodiment, n4 is 5.
In one embodiment, at least one $R_{41}$ is halogen (e.g., F, Cl, Br, or I).
In one embodiment, at least one $R_{41}$ is OH.
In one embodiment, at least one $R_{41}$ is unsubstituted or substituted straight-chain $C_1$-$C_6$ alkyl or branched $C_3$-$C_6$ alkyl. In a further embodiment, at least one $R_{41}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{41}$ is unsubstituted or substituted straight-chain $C_1$-$C_6$ alkoxy or branched $C_3$-$C_6$ alkoxy. In a further embodiment, at least one $R_{41}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).
In one embodiment, m4 is 0, 1, or 2.
In one embodiment, m4 is 0.
In one embodiment, m4 is 1.
In one embodiment, m4 is 2.
In one embodiment, m4 is 3.
In one embodiment, m4 is 4.
In one embodiment, at least one $R_{42}$ is halogen (e.g., F, Cl, Br, or I).
In one embodiment, at least one $R_{42}$ is OH.
In one embodiment, at least one $R_{42}$ is unsubstituted or substituted straight-chain $C_1$-$C_6$ alkyl or branched $C_3$-$C_6$ alkyl. In a further embodiment, at least one $R_{42}$ is methyl, ethyl, propyl, i-propyl, butyl, i-butyl, t-butyl, pentyl, or hexyl, each of which is optionally substituted with halogen (e.g., F, Cl, Br, or I).
In one embodiment, at least one $R_{42}$ is unsubstituted or substituted straight-chain $C_1$-$C_6$ alkoxy or branched $C_3$-$C_6$ alkoxy. In a further embodiment, at least one $R_{42}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).
In one embodiment, o4 is 0, 1, or 2.
In one embodiment, o4 is 0.
In one embodiment, o4 is 1.
In one embodiment, o4 is 2.
In one embodiment, o4 is 3.
In one embodiment, o4 is 4.
In one embodiment, at least one $R_{43}$ is halogen (e.g., F, Cl, Br, or I).
In one embodiment, at least one $R_{43}$ is OH.
In one embodiment, at least one $R_{43}$ is unsubstituted or substituted straight-chain $C_1$-$C_6$ alkyl or branched $C_3$-$C_6$ alkyl. In a further embodiment, at least one $R_{43}$ is methyl, ethyl, propyl, i-propyl, butyl, i-butyl, t-butyl, pentyl, or hexyl, each of which is optionally substituted with halogen (e.g., F, Cl, Br, or I).
In one embodiment, at least one $R_{43}$ is unsubstituted or substituted straight-chain $C_1$-$C_6$ alkoxy or branched $C_3$-$C_6$ alkoxy. In a further embodiment, at least one $R_{43}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).
In one embodiment, p4 is 0, 1, or 2.
In one embodiment, p4 is 0.
In one embodiment, p4 is 1.
In one embodiment, p4 is 2.
In one embodiment, p4 is 3.
In one embodiment, p4 is 4.
In one embodiment, p4 is 5.
In one embodiment, at least one $R_{44}$ is halogen (e.g., F, Cl, Br, or I).
In one embodiment, at least one $R_{44}$ is OH.
In one embodiment, at least one $R_{44}$ is unsubstituted or substituted straight-chain $C_1$-$C_6$ alkyl or branched $C_3$-$C_6$ alkyl. In a further embodiment, at least one $R_{44}$ is methyl, ethyl, propyl, i-propyl, butyl, i-butyl, t-butyl, pentyl, or hexyl, each of which is optionally substituted with halogen (e.g., F, Cl, Br, or I). In a further embodiment, at least one $R_{44}$ is methyl In one embodiment, at least one $R_{44}$ is unsubstituted or substituted straight-chain $C_1$-$C_6$ alkoxy or branched $C_3$-$C_6$ alkoxy. In a further embodiment, at least one $R_{44}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{44}$ is $(CH_2)_{q4}$—$NH_2$, $(CH_2)_{q4}$—NH—$C_1$-$C_6$ alkyl, or $(CH_2)_{q4}$—$N(C_1$-$C_6$ alkyl$)_2$, wherein the $C_1$-$C_6$ alkyl is methyl, ethyl, propyl, i-propyl, butyl, i-butyl, t-butyl, pentyl, or hexyl, each of which is optionally substituted with halogen (e.g., F, Cl, Br, or I). In a further embodiment, at least one $R_{44}$ is $(CH_2)_{q4}$—NH—$C_1$-$C_6$ alkyl.

In one embodiment, q4 is 0, 1, 2, or 3.
In one embodiment, q4 is 0.
In one embodiment, q4 is 1.
In one embodiment, q4 is 2.
In one embodiment, q4 is 3.
In one embodiment, q4 is 4.
In one embodiment, q4 is 5.
In one embodiment, q4 is 6.

Any of the groups described above for any of $Z_1$, $Z_2$, R, $R_{41}$, $R_{42}$, $R_{43}$, $R_{44}$, n4, m4, o4, p4, and q4 can be combined with any of the groups described above for one or more of the remainder of $Z_1$, $Z_2$, R, $R_{41}$, $R_{42}$, $R_{43}$, $R_{44}$, n4, m4, o4, p4, and q4.

In one embodiment, $Z_1$-$Z_2$ is C(O)—O or O—C(O); n4, m4, and o4 are each 0; and p4 is 0, 1, or 2. In a further embodiment, p4 is 2.

In one embodiment, $Z_1$-$Z_2$ is C(O)—O; n4, m4, and o4 are each 0; and p4 is 0, 1, or 2. In a further embodiment, p4 is 2.

In one embodiment, $Z_1$-$Z_2$ is C(O)—S or S—C(O); n4, m4, and o4 are each 0; and p4 is 0, 1, or 2. In a further embodiment, p4 is 2.

In one embodiment, $Z_1$-$Z_2$ is C(O)—S; n4, m4, and o4 are each 0; and p4 is 0, 1, or 2. In a further embodiment, p4 is 2.

In one embodiment, $Z_1$-$Z_2$ is C(O)—NH—NH or NH—NH—C(O); n4, m4, and o4 are each 0; and p4 is 0, 1, or 2. In a further embodiment, p4 is 2.

In one embodiment, $Z_1$-$Z_2$ is C(O)—NH; n4, m4, and o4 are each 0; and p4 is 0, 1, or 2. In a further embodiment, p4 is 2.

In one embodiment, a compound of formula A is a compound of formula V:

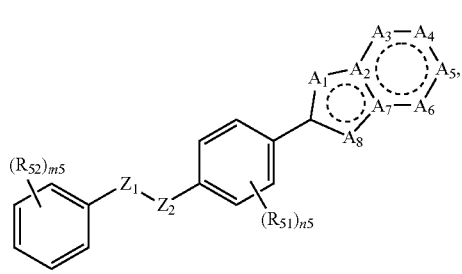

(V)

or a pharmaceutically acceptable salt thereof, wherein:
$Z_1$-$Z_2$ is C(O)—O, O—C(O), C(O)—S, S—C(O), C(O)—NR—NR, or NR—NR—C(O);
each R is independently H or $C_1$-$C_3$ alkyl;
$A_1$, $A_3$, $A_4$, $A_5$, $A_6$, and $A_8$ are each independently N, $NR_{53}$, or $CR_{53}$;

$A_2$ and $A_7$ are each independently N or C;
each $R_{53}$ is independently H, halogen, OH, unsubstituted or substituted $C_1$-$C_6$ alkyl, or unsubstituted or substituted $C_1$-$C_6$ alkoxy;
n5 is 0, 1, 2, 3, or 4;
each $R_{51}$ is independently halogen, OH, unsubstituted or substituted $C_1$-$C_6$ alkyl, or unsubstituted or substituted $C_1$-$C_6$ alkoxy;
m5 is 0, 1, 2, 3, 4, or 5; and
each $R_{52}$ is independently halogen, OH, unsubstituted or substituted $C_1$-$C_6$ alkyl, or unsubstituted or substituted $C_1$-$C_6$ alkoxy.

In one embodiment, $Z_1$-$Z_2$ is C(O)—O, O—C(O), C(O)—S, or S—C(O).

In one embodiment, $Z_1$-$Z_2$ is C(O)—S, S—C(O), C(O)—NR—NR, or NR—NR—C(O).

In one embodiment, $Z_1$-$Z_2$ is C(O)—O or O—C(O).
In one embodiment, $Z_1$-$Z_2$ is C(O)—O.
In one embodiment, $Z_1$-$Z_2$ is C(O)—S or S—C(O).
In one embodiment, $Z_1$-$Z_2$ is C(O)—S.
In one embodiment, $Z_1$-$Z_2$ is C(O)—NR—NR or NR—NR—C(O).
In one embodiment, $Z_1$-$Z_2$ is C(O)—NR—NR.

In one embodiment, each R is H (i.e., $Z_1$-$Z_2$ is C(O)—NH—NH or NH—NH—C(O)).

In one embodiment, one of R is H, and the other R is $C_1$-$C_3$ alkyl (e.g., methyl, ethyl, or propyl).

In one embodiment, each R is $C_1$-$C_3$ alkyl (e.g., methyl, ethyl, or propyl).

In one embodiment, $A_1$, $A_3$, $A_4$, $A_5$, $A_6$, and $A_8$ are each $CR_{53}$.

In one embodiment, one of $A_1$, $A_3$, $A_4$, $A_5$, $A_6$, and $A_8$ is N or $NR_{53}$, and the remainder of $A_1$, $A_3$, $A_4$, $A_5$, $A_6$, and $A_8$ are $CR_{53}$.

In one embodiment, two of $A_1$, $A_3$, $A_4$, $A_5$, $A_6$, and $A_8$ are N or $NR_{53}$, and the remainder of $A_1$, $A_3$, $A_4$, $A_5$, $A_6$, and $A_8$ are $CR_{53}$.

In one embodiment, three of $A_1$, $A_3$, $A_4$, $A_5$, $A_6$, and $A_8$ are N or $NR_{53}$, and the remainder of $A_1$, $A_3$, $A_4$, $A_5$, $A_6$, and $A_8$ are $CR_{53}$.

In one embodiment, four of $A_1$, $A_3$, $A_4$, $A_5$, $A_6$, and $A_8$ are N or $NR_{53}$, and the remainder of $A_1$, $A_3$, $A_4$, $A_5$, $A_6$, and $A_8$ are $CR_{53}$.

In one embodiment, five of $A_1$, $A_3$, $A_4$, $A_5$, $A_6$, and $A_8$ are N or $NR_{53}$, and the remainder of $A_1$, $A_3$, $A_4$, $A_5$, $A_6$, and $A_8$ is $CR_{53}$.

In one embodiment, $A_2$ and $A_7$ are each N.
In one embodiment, one of $A_2$ and $A_7$ is N, and the other is C.
In one embodiment, $A_2$ and $A_7$ are each C.
In one embodiment, at least one $R_{53}$ is halogen (e.g., F, Cl, Br, or I).
In one embodiment, at least one $R_{53}$ is OH.

In one embodiment, at least one $R_{53}$ is unsubstituted or substituted straight-chain $C_1$-$C_6$ alkyl or branched $C_3$-$C_6$ alkyl. In a further embodiment, at least one $R_{53}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{53}$ is unsubstituted or substituted straight-chain $C_1$-$C_6$ alkoxy or branched $C_3$-$C_6$ alkoxy. In a further embodiment, at least one $R_{53}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, n5 is 0, 1, or 2.
In one embodiment, n5 is 0.
In one embodiment, n5 is 1.

In one embodiment, n5 is 2.

In one embodiment, n5 is 3.

In one embodiment, n5 is 4.

In one embodiment, at least one $R_{51}$ is halogen (e.g., F, Cl, Br, or I).

In one embodiment, at least one $R_{51}$ is OH.

In one embodiment, at least one $R_{51}$ is unsubstituted or substituted straight-chain $C_1$-$C_6$ alkyl or branched $C_3$-$C_6$ alkyl. In a further embodiment, at least one $R_{51}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{51}$ is unsubstituted or substituted straight-chain $C_1$-$C_6$ alkoxy or branched $C_3$-$C_6$ alkoxy. In a further embodiment, at least one $R_{51}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, m5 is 0, 1, or 2.

In one embodiment, m5 is 0.

In one embodiment, m5 is 1.

In one embodiment, m5 is 2.

In one embodiment, m5 is 3.

In one embodiment, m5 is 4.

In one embodiment, m5 is 5.

In one embodiment, at least one $R_{52}$ is halogen (e.g., F, Cl, Br, or I).

In one embodiment, at least one $R_{52}$ is OH.

In one embodiment, at least one $R_{52}$ is unsubstituted or substituted straight-chain $C_1$-$C_6$ alkyl or branched $C_3$-$C_6$ alkyl. In a further embodiment, at least one $R_{52}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{52}$ is unsubstituted or substituted straight-chain $C_1$-$C_6$ alkoxy or branched $C_3$-$C_6$ alkoxy. In a further embodiment, at least one $R_{52}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

Any of the groups described above for any of $Z_1$, $Z_2$, R, $A_1$, $A_2$, $A_3$, $A_4$, $A_5$, $A_6$, $A_7$, As, $R_{51}$, $R_{52}$, $R_{53}$, n5, and m5 can be combined with any of the groups described above for one or more of the remainder of $Z_1$, $Z_2$, R, $A_1$, $A_2$, $A_3$, $A_4$, $A_5$, $A_6$, $A_7$, $A_8$, $R_{51}$, $R_{52}$, $R_{53}$, n5, and m5.

In one embodiment, a compound of formula V is a compound of formula Va:

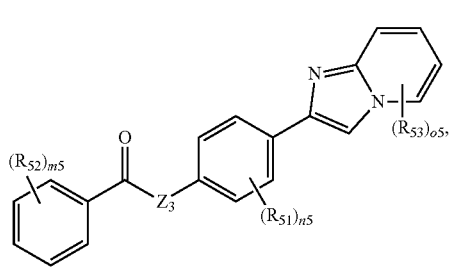

or a pharmaceutically acceptable salt thereof, wherein:
$Z_3$ is O, S, or NR—NR;
o5 is 0, 1, 2, 3, 4, or 5; and
R, $R_{51}$, $R_{52}$, $R_{53}$, n5, and m5 are each as defined above in formula V.

In one embodiment, $Z_3$ is O.

In one embodiment, $Z_3$ is S.

In one embodiment, $Z_3$ is NR.

In one embodiment, o5 is 0, 1, or 2.

In one embodiment, o5 is 0.

In one embodiment, o5 is 1.

In one embodiment, o5 is 2.

In one embodiment, o5 is 3.

In one embodiment, o5 is 4.

In one embodiment, o5 is 5.

In one embodiment, n5 is 0 or 1.

In one embodiment, m5 is 0 or 1.

Any of $Z_3$, R, $R_{51}$, $R_{52}$, $R_{53}$, n5, m5, and o5 can be selected from any of the groups described above and combined with any of the groups described above for one or more of the remainder of $Z_3$, R, $R_{51}$, $R_{52}$, $R_{53}$, n5, m5, and o5.

The present application provides a compound of a compound of formula (VI):

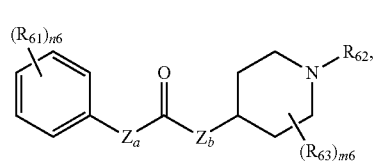

or a pharmaceutically acceptable salt thereof, wherein:
Za and Zb are each independently 0 or NR, wherein at least one of Za and Zb is 0;
R is H or $C_1$-$C_3$ alkyl;
n6 is 0, 1, 2, 3, 4, or 5;
each $R_{61}$ is independently halogen, cyano, OH, unsubstituted or substituted $C_1$-$C_6$ alkyl, or unsubstituted or substituted $C_1$-$C_6$ alkoxy;
$R_{62}$ is unsubstituted or substituted $C_1$-$C_6$ alkyl;
m6 is 0, 1, 2, 3, or 4; and
each $R_{63}$ is independently halogen, cyano, OH, unsubstituted or substituted $C_1$-$C_6$ alkyl, unsubstituted or substituted $C_1$-$C_6$ alkoxy, unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S.

In one embodiment, Za is O and Zb is NR.

In one embodiment, Za is NR and Zb is O

In one embodiment, Za is O and Zb is O.

In one embodiment, R is H.

In one embodiment, R is $C_1$-$C_3$ alkyl (e.g., methyl, ethyl, or propyl).

In one embodiment, n6 is 0, 1, or 2.

In one embodiment, n6 is 0.

In one embodiment, n6 is 1.

In one embodiment, n6 is 2.

In one embodiment, n6 is 3.

In one embodiment, n6 is 4.

In one embodiment, n6 is 5.

In one embodiment, at least one $R_{61}$ is halogen (e.g., F, Cl, Br, or I).

In one embodiment, at least one $R_{61}$ is cyano.

In one embodiment, at least one $R_{61}$ is OH.

In one embodiment, at least one $R_{61}$ is unsubstituted or substituted straight-chain $C_1$-$C_6$ alkyl or branched $C_3$-$C_6$ alkyl. In a further embodiment, at least one $R_{61}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{61}$ is unsubstituted or substituted straight-chain $C_1$-$C_6$ alkoxy or branched $C_3$-$C_6$ alkoxy. In a further embodiment, at least one $R_{61}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, $R_{62}$ is unsubstituted or substituted straight-chain $C_1$-$C_6$ alkyl or branched $C_3$-$C_6$ alkyl. In a further embodiment, $R_{62}$ is methyl, ethyl, propyl, i-propyl, butyl, i-butyl, t-butyl, pentyl, or hexyl, each of which is optionally substituted with halogen (e.g., F, Cl, Br, or I).

In one embodiment, m6 is 0, 1, or 2.
In one embodiment, m6 is 0.
In one embodiment, m6 is 1.
In one embodiment, m6 is 2.
In one embodiment, m6 is 3.
In one embodiment, m6 is 4.

In one embodiment, at least one $R_{63}$ is halogen (e.g., F, Cl, Br, or I), cyano, OH, unsubstituted or substituted $C_1$-$C_6$ alkyl, or unsubstituted or substituted $C_1$-$C_6$ alkoxy.

In one embodiment, at least one $R_{63}$ is halogen (e.g., F, Cl, Br, or I).

In one embodiment, at least one $R_{63}$ is cyano.
In one embodiment, at least one $R_{63}$ is OH.
In one embodiment, at least one $R_{63}$ is unsubstituted or substituted straight-chain $C_1$-$C_6$ alkyl or branched $C_3$-$C_6$ alkyl. In a further embodiment, at least one $R_{63}$ is methyl, ethyl, propyl, i-propyl, butyl, i-butyl, t-butyl, pentyl, or hexyl, each of which is optionally substituted with halogen (e.g., F, Cl, Br, or I).

In one embodiment, at least one $R_{63}$ is unsubstituted or substituted straight-chain $C_1$-$C_6$ alkoxy or branched $C_3$-$C_6$ alkoxy. In a further embodiment, at least one $R_{63}$ is methoxy, ethoxy, propoxy, i-propoxy, butoxy, i-butoxy, t-butoxy, pentoxy, or hexyloxy, each of which is optionally substituted with halogen (e.g., F, Cl, Br, or I).

In one embodiment, at least one $R_{63}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S.

In one embodiment, at least one $R_{63}$ is $C_3$-$C_8$ cycloalkyl selected from cyclopropyl, cyclobutyl, cyclopentyl, cyclohexyl, cycloheptyl, and cyclooctyl, each of which is optionally substituted with one or more substituents independently selected from halogen, OH, cyano, nitro, $C_1$-$C_6$ alkyl, $C_1$-$C_6$ alkoxy, and amino.

In one embodiment, at least one $R_{63}$ is phenyl optionally substituted with one or more substituents independently selected from halogen, OH, cyano, nitro, $C_1$-$C_6$ alkyl, $C_1$-$C_6$ alkoxy, and amino.

In one embodiment, at least one $R_{63}$ is heterocyclyl optionally substituted with one or more substituents independently selected from halogen, OH, cyano, nitro, $C_1$-$C_6$ alkyl, $C_1$-$C_6$ alkoxy, and amino. In a further embodiment, at least one $R_{63}$ is heterocyclyl comprising a 5- or 6-membered ring optionally substituted with one or more substituents independently selected from halogen, OH, cyano, nitro, $C_1$-$C_6$ alkyl, $C_1$-$C_6$ alkoxy, and amino.

In one embodiment, at least one $R_{63}$ is heteroaryl optionally substituted with one or more substituents independently selected from halogen, OH, cyano, nitro, $C_1$-$C_6$ alkyl, $C_1$-$C_6$ alkoxy, and amino. In a further embodiment, at least one $R_{63}$ is heteroaryl selected from pyrrolyl, imidazolyl, pyrazolyl, pyridinyl, pyrimidinyl, indolyl, and benzoimidazolyl, each of which is optionally substituted with one or more substituents independently selected from halogen, OH, cyano, nitro, $C_1$-$C_6$ alkyl, $C_1$-$C_6$ alkoxy, and amino. In a further embodiment, at least one $R_{63}$ is benzoimidazolyl.

Any of the groups described above for any of Za, Zb, R, $R_{61}$, $R_{62}$, $R_{63}$, n6, and m6 can be combined with any of the groups described above for one or more of the remainder of Za, Zb, R, $R_{61}$, $R_{62}$, $R_{63}$, n6, and m6.

In one embodiment, Za is O and Zb is NH; n6 is 0 or 1; m6 is 0 or 1; and $R_{63}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{62}$ is methyl. In a further embodiment, at least one $R_{63}$ is unsubstituted or substituted heteroaryl comprising one or two 5- to 8-membered rings and 1-4 heteroatoms selected from O, N, and S. In a further embodiment, at least one $R_{63}$ is benzoimidazolyl. In a further embodiment, at least one $R_{63}$ is benzoimidazolyl. In a further embodiment, at least one $R_{61}$ is cyano.

In one embodiment, Za is NH and Zb is O; n6 is 0 or 1; m6 is 0 or 1; and $R_{63}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S. In a further embodiment, $R_{62}$ is methyl. In a further embodiment, at least one $R_{63}$ is unsubstituted or substituted heteroaryl comprising one or two 5- to 8-membered rings and 1-4 heteroatoms selected from O, N, and S. In a further embodiment, at least one $R_{63}$ is benzoimidazolyl. In a further embodiment, at least one $R_{61}$ is cyano.

In one embodiment, a compound of formula (VI) is a compound of formula (VIa):

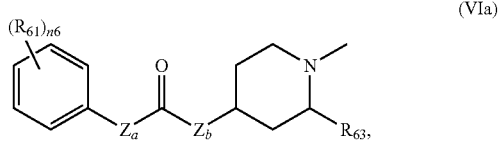

(VIa)

or a pharmaceutically acceptable salt thereof, wherein Za, Zb, R, $R_{61}$, $R_{63}$, and n6 are each as defined above in formula (VI).

In one embodiment, n6 is 1.

In one embodiment, at least one $R_{61}$ is at the para-position of the phenyl ring. In one embodiment, at least one $R_{61}$ is cyano.

In one embodiment, $R_{63}$ is heteroaryl optionally substituted with one or more substituents independently selected from halogen, OH, cyano, nitro, $C_1$-$C_6$ alkyl, $C_1$-$C_6$ alkoxy, and amino. In a further embodiment, at least one $R_{63}$ is heteroaryl selected from pyrrolyl, imidazolyl, pyrazolyl, pyridinyl, pyrimidinyl, indolyl, and benzoimidazolyl, each of which is optionally substituted with one or more substituents independently selected from halogen, OH, cyano, nitro, $C_1$-$C_6$ alkyl, $C_1$-$C_6$ alkoxy, and amino. In a further embodiment, at least one $R_{63}$ is benzoimidazolyl.

Any of Za, Zb, R, $R_{61}$, $R_{63}$, and n6 can be selected from any of the groups described above and combined with any of the groups described above for one or more of the remainder of Za, Zb, R, $R_{61}$, $R_{63}$, and n6.

It will be understood that the above classes may be combined to form additional classes, as for example the combination of selections of two or more substituents.

Representative compounds of the present application include compounds listed in

TABLE 1

| Cmpd No. | Structure |
|---|---|
| 1-3 | 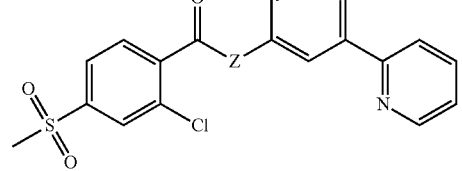<br>Z is O (1), S (2), or NH-NH (3) |
| 4-6 | 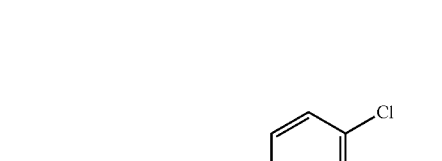<br>Z is O (4), S (5), or NH-NH (6) |
| 7-9 | 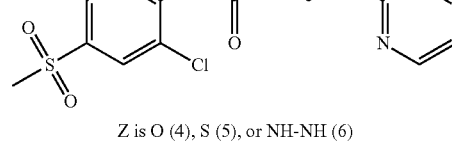<br>Z is O (7), S (8), or NH-NH (9) |
| 10-12 | 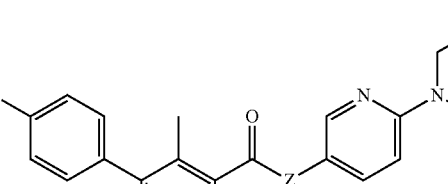<br>Z is O (10), S (11), or NH-NH (12) |

TABLE 1-continued
| Cmpd No. | Structure |
|---|---|
| 13-15 | 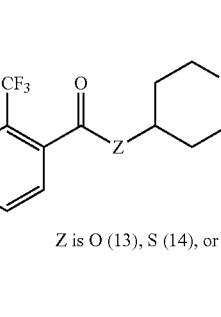<br>Z is O (13), S (14), or NH-NH (15) |
| 16-18 | 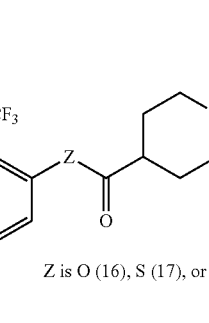<br>Z is O (16), S (17), or NH-NH (18) |
| 19-21 | 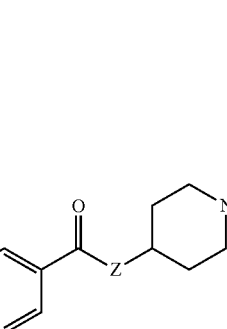<br>Z is O (19), S (20), or NH-NH (21) |
| 22-24 | 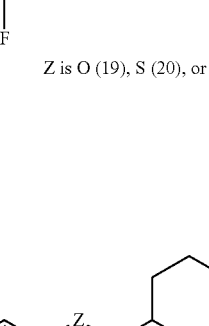<br>Z is O (22), S (23), or NH-NH (24) |

TABLE 1-continued
| Cmpd No. | Structure |
|---|---|
| 25-27 | 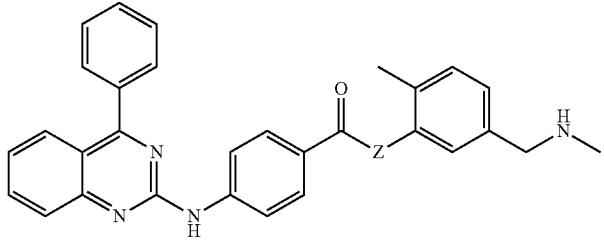<br>Z is O (25), S (26), or NH-NH (27) |
| 28-30 | 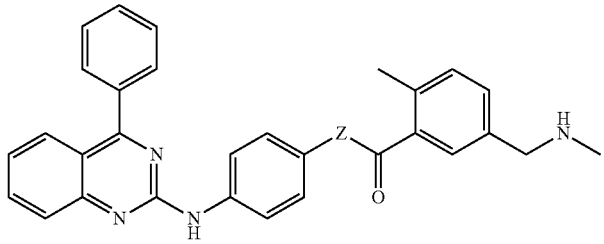<br>Z is O (28), S (29), or NH-NH (30) |
| 31-33 | 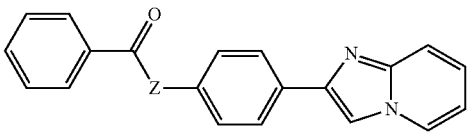<br>Z is O (31), S (32), or NH-NH (33) |
| 34-36 | 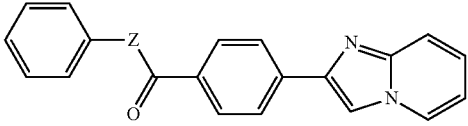<br>Z is O (34), S (35), or NH-NH (36) |
| 37 | 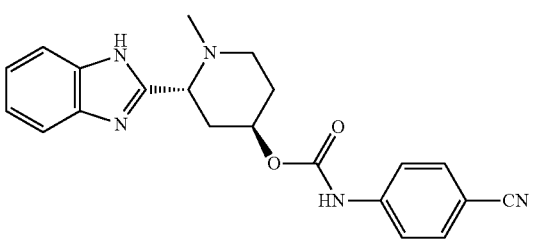 [SMILES: CN1CC[C@@H](OC(=O)Nc2ccc(C#N)cc2)C[C@@H]1c1nc2ccccc2[nH]1] |
| 38 | 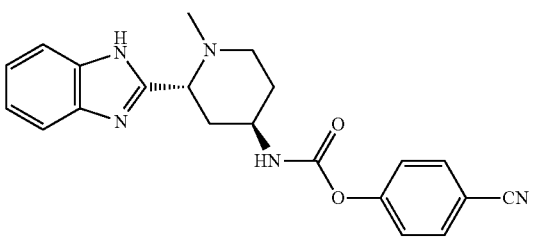 [SMILES: CN1CC[C@@H](NC(=O)Oc2ccc(C#N)cc2)C[C@@H]1c1nc2ccccc2[nH]1] |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include Cl, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl and n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" or "substituted $C_1$-$C_6$ alkyl" refers to alkyl moieties having substituents replacing one or more hydrogen atoms on one or more carbons of the hydrocarbon backbone. Such substituents can include, for example, alkyl, cycloalkyl, alkenyl, alkynyl, aryl, heteroaryl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, aryloxyl, phosphate, phosphonato, phosphinato, amino (including $NH_2$, monoalkylamino e.g., $NH(C_1-C_6)$alkyl, dialkylamino e.g., $N[(C_1-C_6)alkyl]_2$, arylamino, diarylamino and alkylarylamino), acylamino (including alkylcarbonylamino, arylcarbonylamino, carbamoyl and ureido), amidino, imino, sulfhydryl, SH, alkylthio, arylthio, thiocarboxylate, sulfates, alkylsulfinyl, sulfonato, sulfamoyl, sulfonamido, nitro, trifluoromethyl, $CH_2$, F, $CHF_2$, $OCF_3$, cyano, azido, heterocyclyl, alkylaryl, or an aromatic or heteroaromatic moiety. Cycloalkyls can be further substituted, e.g., with the substituents described above.

"Aryl" includes groups with aromaticity, including "conjugated", or multicyclic, systems with at least one aromatic ring. Examples include phenyl, napthalene, etc. The term "$C_6$-$C_{10}$" includes aryl groups containing six to ten carbon atoms.

"Heteroaryl" groups are groups with aromaticity, including "conjugated", or multicyclic, systems with at least one aromatic ring having from one to four heteroatoms in the ring structure, and may also be referred to as "aryl heterocycles" or "heteroaromatics". A heteroaryl group can be partially aromatic, i.e., not all of the rings are aromatic. As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1, 2, or 3 or 1, 2, 3, or 4 or 1, 2, 3, 4, or 5 or 1, 2, 3, 4, 5, or 6 heteroatoms, independently selected from the group consisting of nitrogen, oxygen and sulfur. In one aspect, a heteroaryl comprises one or two 5- or 6-membered rings and 1-4 heteroatoms selected from N, O and S. For an "unsubstituted heteroaryl", the nitrogen atom may be substituted or unsubstituted (i.e., N or NR wherein R is H). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, quinoline, benzofuran, benzoimidazole, imidazopyridine, thiophene, indole, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). In one aspect, a heterocycle comprises one, two, or three 5- or 6-membered saturated rings and 1-4 heteroatoms selected from N, O and S. In another aspect, a heterocycle comprises one, two, or three 5- or 6-membered partially saturated and/or saturated rings and 1-4 heteroatoms selected from N, O and S. In one aspect, a heterocycle comprises spiro rings. Examples of heterocycles include, but are not limited to, morpholine, pyrrolidine, tetrahydrothiophene, piperidine, piperazine and tetrahydrofuran.

Additional examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_4$) occurs more than one time in any constituent or formula for a compound, its definition at each occurrence is independent of its definition at every other occurrence. Thus, for example, if a group is shown to be substituted with 0-2 $R_4$ moieties, then the group may optionally be substituted with up to two $R_4$ moieties and $R_4$ at each occurrence is selected independently from the definition of $R_4$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkoxy" or "alkoxyl" includes substituted and unsubstituted alkyl, alkenyl and alkynyl groups covalently linked to an oxygen atom. "$C_1$-$C_6$ alkoxy" includes alkoxy groups with an alkyl group having one, two, three, four, five, or six carbon atoms. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ester" includes compounds or moieties which contain a carbon bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioester" includes compounds or moieties which contain a carbon bound to a sulfur atom which is bonded to the carbon of a carbonyl group.

As used herein, "amine" or "amino" or "$NH_2$" includes moieties where a nitrogen atom is covalently bonded to at least one carbon or heteroatom. "Alkylamino" or "monoalkylamino" includes groups of compounds wherein nitrogen is bound to at least one alkyl group. "$NH(C_1$-$C_6)$ alkyl" is an alkylamino group having an alkyl group with one, two, three, four, five, or six carbon atoms. Examples of alkylamino groups include benzylamino, methylamino, ethylamino, phenethylamino, etc. "Dialkylamino" includes groups wherein the nitrogen atom is bound to at least two additional alkyl groups. "N[($C_1$-$C_6$) alkyl]" is a dialkylamino group having two alkyl groups each with one, two, three, four, five, or six carbon atoms. The two alkyl groups are the same or different. Examples of dialkylamino groups include, but are not limited to, dimethylamino and diethylamino.

The term "amide" or "aminocarboxy" includes compounds or moieties that contain a nitrogen atom that is bound to the carbon of a carbonyl or a thiocarbonyl group.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present application includes all isomers, such as geometrical isomers, optical isomers based on an asymmetrical carbon, stereoisomers, tautomers, and the like. In addition, a crystal polymorphism may be present for the compounds represented by the formulae presented herein. It is noted that any crystal form, crystal form mixture, or anhydride or hydrate thereof is included in the scope of the present application. Furthermore, so-called metabolite which is produced by degradation of the present compound in vivo is included in the scope of the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form. Tautomeric forms of the compounds of each of the formulae described herein are included in the present application.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^3$H, $^{11}$C, $^{14}$C, $^2$H and $^{18}$F.

Compounds of each of the formulae described herein or pharmaceutically acceptable salts thereof, that contain the aforementioned isotopes and/or other isotopes of other atoms are within the scope of the present application. Isotopically-labeled compounds of the present application, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are useful for their ease of preparation and detectability. $^{11}$C and $^{18}$F isotopes are useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled compounds of the formulae described herein or pharmaceutically acceptable salts, tautomers, prodrugs, solvates, metabolites, polymorphs, analogs or derivatives thereof, can generally be prepared by carrying out the procedures disclosed in the Schemes and/or in the Examples described herein, by substituting a readily available isotopically labeled reagent for a non-isotopically labeled reagent. In one embodiment, the compounds of the formulae described herein or pharmaceutically acceptable salts, tautomers, prodrugs, solvates, metabolites, polymorphs, analogs or derivatives thereof, are not isotopically labelled.

2. Synthesis of Compounds of the Present Application

The present application provides methods for the synthesis of the compounds of each of the formulae described herein or pharmaceutically acceptable salts thereof. The present application also provides detailed methods for the synthesis of various disclosed compounds of each of the formulae described herein or pharmaceutically acceptable salts thereof according to the following schemes and/or as shown in the examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the application remains operable. Moreover, two or more steps or actions can be conducted simultaneously.

The synthetic processes of the application can tolerate a wide variety of functional groups in the compounds prepared, therefore various substituted starting materials can be used. The processes generally provide the desired final compound at or near the end of the overall process, although it may be desirable in certain instances to further convert the compound to a pharmaceutically acceptable salt thereof.

Compounds of the present application or pharmaceutically acceptable salts thereof can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry*: Reactions, Mechanisms, and Structure, 5$^{th}$ edition, John Wiley & Sons: New York, 2001; and Greene, T. W., Wuts, P. G. M., *Protective Groups in Organic Synthesis*, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application or pharmaceutically acceptable salts, tautomers, prodrugs, solvates, metabolites, polymorphs, analogs or derivatives thereof.

Compounds of the present application can be conveniently prepared by a variety of methods familiar to those skilled in the art. The compounds each of the formulae described herein may be prepared according to the following procedures from commercially available starting materials or starting materials which can be prepared using literature procedures. These procedures show the preparation of representative compounds of this application.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

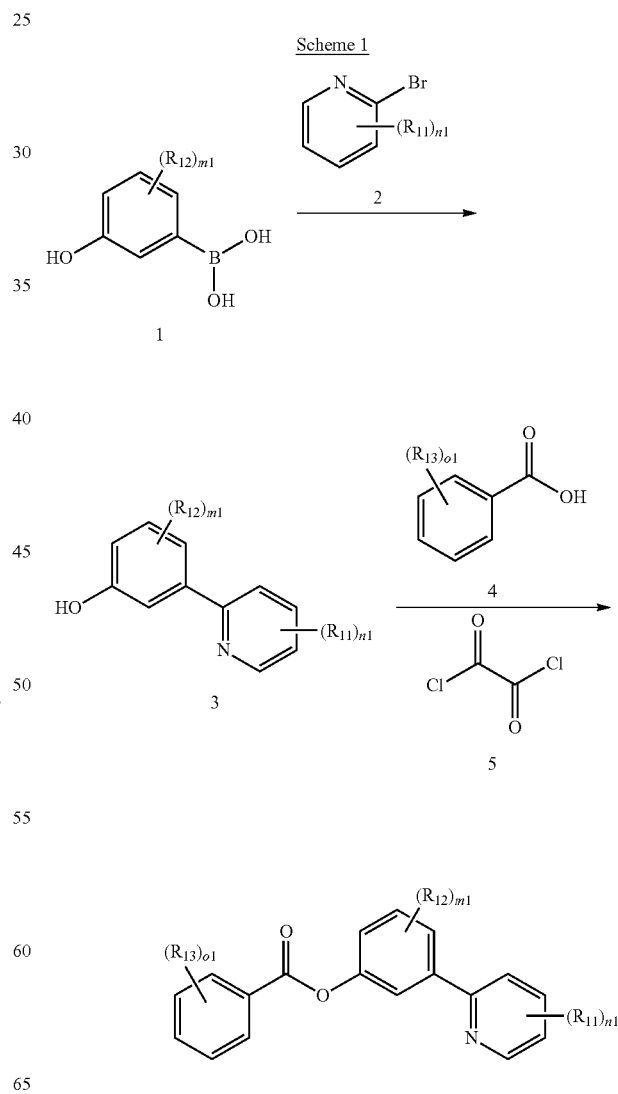

Scheme 2:
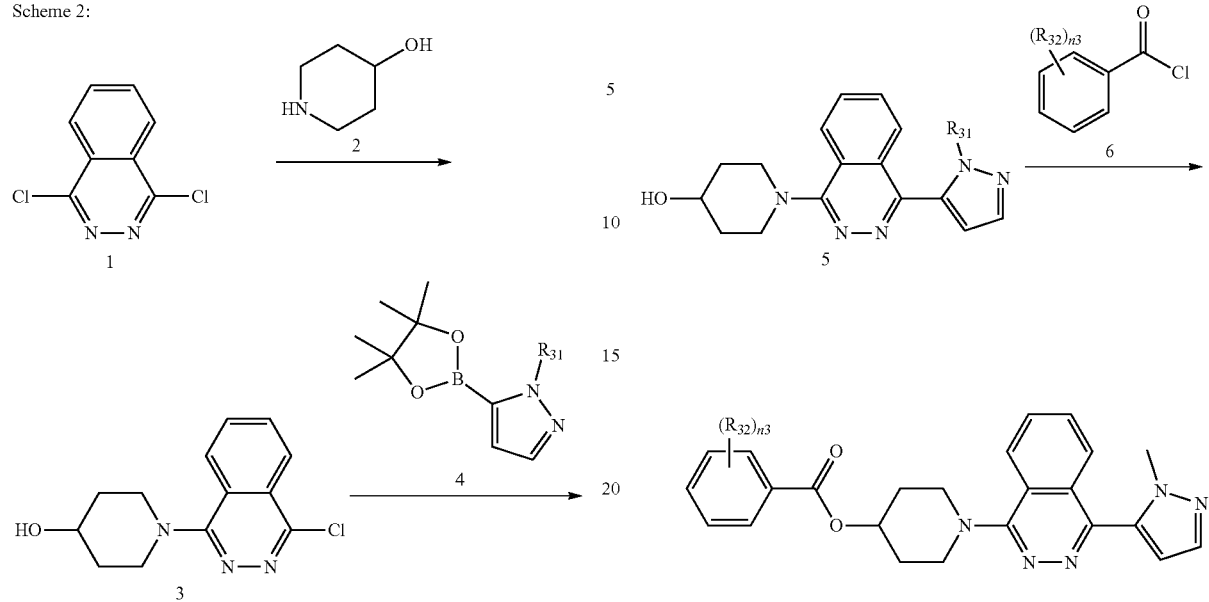

Scheme 3:
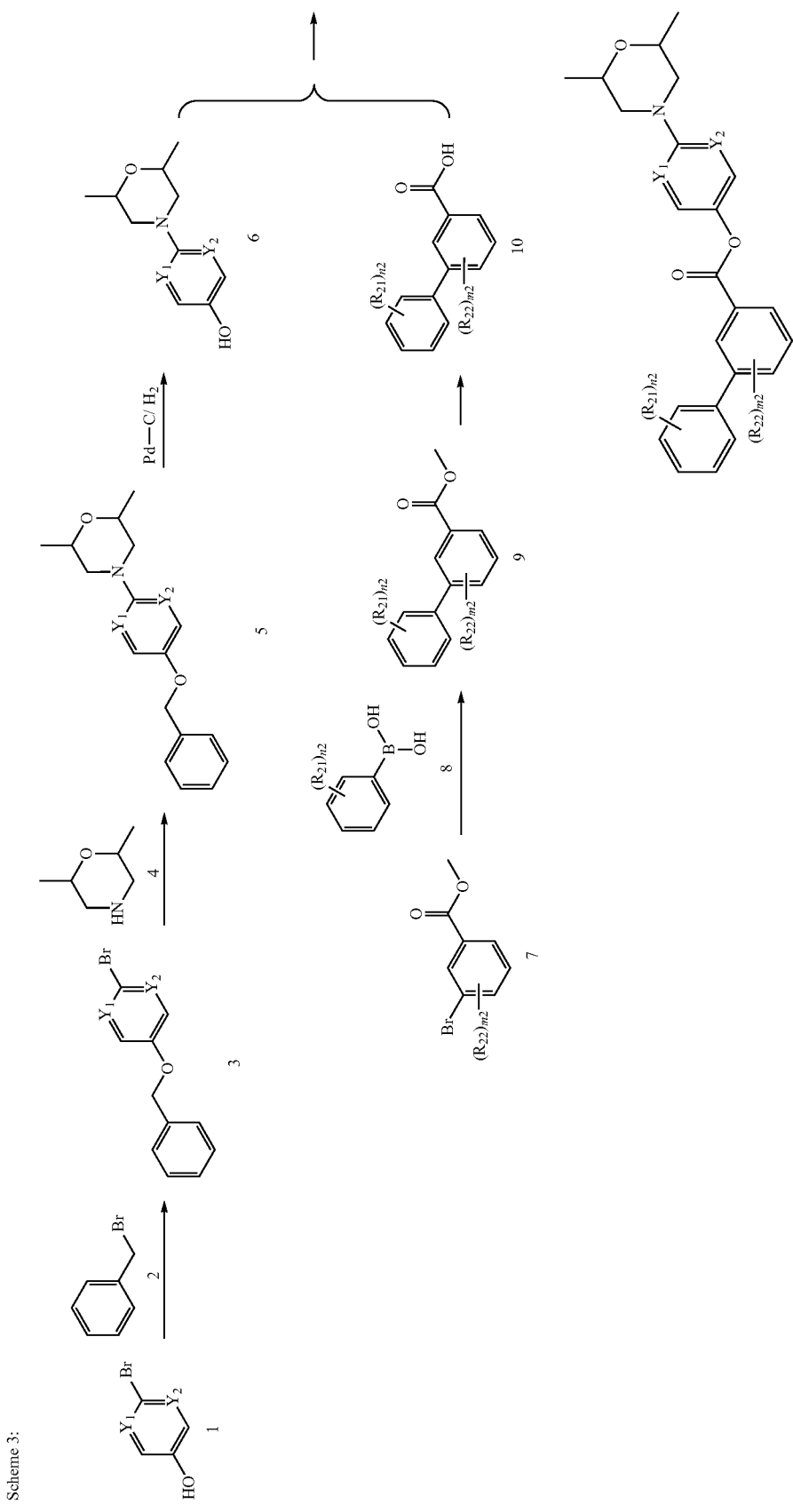

The physicochemical properties and biological activities of the compounds of the present application can be assessed using methods and materials known in the art. For example, the stability of the compounds may be evaluated by incubating the compounds of the present application with serum for various periods of time and then measuring the remaining amount of the compounds through common analytic methods, such as mass spectrometry (e.g., LC-MS). In another example, the cell growth inhibitory activity of the compounds of the present application may be assessed by treating cancer cells with various concentrations of the compounds for different time periods, and then measuring the number of viable cells by common techniques, such as luminescence assays. In addition, the ability of the compounds of the present application to regulate the Hh signaling pathway may be determined by treating cells with the compounds of the present application and then measuring the expression of the targeted genes (e.g., Gli1 or Ptch) or a reporter gene (e.g., luciferase).

3. Biological Assays

Stability Measurements

SMO antagonists are incubated at selected concentration(s) in serum or serum-free cell culture media at 37° C. for varying lengths of time. Reactions are terminated by cold acetonitrile. Samples are centrifuged and the supernatant is removed and filtered, before measurement by LC-MS. The percent remaining of each compound is calculated by the integrated area of the peak at each time point divided by the peak at the t=0 time point. Data is fit to a one-phase decay curve using GraphPad Prism 6 software.

Cell Viability

Sample cells (e.g., SmoWT-MB cells, a mouse medulloblastoma cell line with wild-type Smo and Ptch1 loss of function) are distributed into culture plates and then pinned with SMO antagonists in quadruplicate over a ten-point dose range. Cell viability, relative to control treated cells, is measured after various time points after treatment (e.g., 24, 48, 72, or 96 hours) by ATPlite. $IC_{50}$ is determined by fitting dose-response curves in GraphPad Prism 6 software.

Gene Expression Analysis

Sample cells (e.g., SmoWT-MB cells) are plated in culture plates, grown for 24 hours, and treated with SMO antagonists for 24 hours. After treatment, RNA is extracted from cells and cDNA is prepared from the RNA. The fold-change in expression for the gene(s) of interest (e.g., Gli1 and Ptch1), relative to control is determined by qRT-PCR using the $\Delta\Delta C_t$ method.

Hh Pathway Cell Reporter Assays

Sample cells (e.g., Shh-LightII cells, NIH-3T3 cells stably expressing Gli-dependent firefly luciferase and constitutively active *Renilla* luciferase) are distributed into culture plates and grown for 48 hours. Cells are changed to serum-free media and Hh pathway activity is stimulated by treatment with Smoothened agonist (SAG). Cells are treated with SMO antagonist for 24 hours (or for 24 hours with an additional dose after 20 hours) and luciferase activity (normalized to *Renilla* luciferase and relative to DMSO treated cells) is measured using the Dual Luciferase Reporter Assay kit (Promega) as a surrogate for Hh pathway activation.

4. Methods of Treatment

The present application provides methods for regulating the Hh signaling pathway, by using a compound of the present application, or a pharmaceutically acceptable salt thereof. In one embodiment, a compound of the present application regulates the Hh signaling pathway by inhibiting or decreasing the activity of SMO. Accordingly, disorders mediated by the Hh signaling pathway (e.g., activity of SMO) can be treated by the compound of the present application, or a pharmaceutically acceptable salt thereof.

The present application provides methods for the treatment of a disorder mediated by the Hh signaling pathway (e.g., the disorders described herein, such as medulloblastoma (MB) and basal cell carcinoma (BCC)) in a subject in need thereof by administering to the subject, a therapeutically effective amount of a compound of the present application, or a pharmaceutically acceptable salt thereof. The disorder can be a cell proliferative disorder, and the cell proliferative disorder can be cancer or a precancerous condition. The present application further provides the use of a compound of the present application, or a pharmaceutically acceptable salt thereof, for the treatment of a disorder mediated by the Hh signaling pathway. The present application further provides the use of a compound of the present application, or a pharmaceutically acceptable salt thereof, for the preparation of a medicament useful for the treatment of a disorder mediated by the Hh signaling pathway.

The present application also provides methods of protecting against a disorder mediated by the Hh signaling pathway (e.g., the disorders described herein, such as medulloblastoma (MB) and basal cell carcinoma (BCC)) in a subject in need thereof by administering to the subject a therapeutically effective amount of compound of the present application, or a pharmaceutically acceptable salt thereof. The disorder can be a cell proliferative disorder, and the cell proliferative disorder can be cancer or a precancerous condition. The present application also provides the use of a compound of the present application, or a pharmaceutically acceptable salt thereof, for the prevention of a disorder mediated by the Hh signaling pathway. The present application also provides the use of a compound of the present application, or a pharmaceutically acceptable salt thereof, for the preparation of a medicament useful for the prevention of a disorder mediated by the Hh signaling pathway.

In one aspect, the compounds or compositions of the present application are administered topically to a subject in need thereof.

As used herein, a "subject in need thereof" is a subject having a disorder mediated by the Hh signaling pathway, or a subject having an increased risk of developing a disorder mediated by the Hh signaling pathway relative to the population at large. A subject in need thereof can have a precancerous condition mediated by the Hh signaling pathway. For example, a subject in need thereof has cancer mediated by the Hh signaling pathway. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells.

The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Examplary disorders mediated by the Hh signaling pathway include, but are not lited to, cancer (e.g., pancreatic cancer, colon cancer, lung cancer, esophageal cancer, gastroesophageal cancer, gastric cancer, breast cancer, ovarian cancer, prostate cancer, skin cancer, leukemias, multiple myeloma, chronic myeloid leukemia, medulloblastoma (MB), basal cell carcinoma (BCC), meningioma, and ameloblastoma), macrocephaly, rib and vertebrae anomalies, intracranial calcification, skeletal abnormalities (e.g., bifid ribs, kyphoscoliosis, early calcification of falx cerebri, sprengel deformity, pectus deformity, polydactyly, syndactyly, or hypertelorism), distinct faces (e.g., frontal and temporoparietal bossing, hypertelorism, mandibular prognathism, cleft lip or palate), eye anomaly (e.g., cataract, coloboma (of the iris, choroid and optic nerve, strabismus, and nystagmus), orbital cyst, microphthalmia, nystagmus), odontogenic keratocysts, hypogonadism, kidney anomalies (e.g., horseshoe kidney, L-shaped kidney, unilateral renal agenesis, renal cyst, and duplication of renal pelvis and ureters), Gorlin syndrome, keratocystic odontogenic tumor, ovarian, and cardio fibroma. In one embodiment, disorders mediated by the Hh signaling pathway are selected from medulloblastoma (MB) and basal cell carcinoma (BCC).

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other non-melanoma malignant growths or lesions of the skin, and metastatic lesions in tissue and organs in the body other than the skin. Cell proliferative disorders of the skin can include hyperplasia, metaplasia, and dysplasia of the skin.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "treating" or "treat" describes the management and care of a patient for the purpose of combating a disease, condition, or disorder and includes the administration of a compound of the present application, or a pharmaceutically acceptable salt thereof, to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviating" or "alleviate" is meant to describe a process by which the severity of a sign or symptom of a disorder is decreased. Importantly, a sign or symptom can be alleviated without being eliminated. In a preferred embodiment, the administration of pharmaceutical compositions of the application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body, but signs are defined as things that can be seen by a doctor, nurse, or other health care professional.

A compound of the present application, or a pharmaceutically acceptable salt thereof, can modulate the activity of a molecular target (e.g., SMO). Modulating refers to stimulating or inhibiting an activity of a molecular target. Preferably, a compound of the present application, or a pharmaceutically acceptable salt thereof, modulates the activity of a molecular target if it stimulates or inhibits the activity of the molecular target by at least 2-fold relative to the activity of the molecular target under the same conditions but lacking only the presence of the compound. More preferably, a compound of the present application, or a pharmaceutically acceptable salt thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of the compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the application 5. Pharmaceutical Compositions The present application also provides pharmaceutical compositions comprising a compound of any of the formulae described herein in combination with at least one pharmaceutically acceptable excipient or carrier.

A "pharmaceutical composition" is a formulation containing the compounds of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, topical, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical composition of the present application may be administered topically. The topical formulation of the present application may be in the form of a solution comprising water and at least one pharmaceutically acceptable excipient. Suitable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-O-cyclodextrin, methyl-β-cyclodextrin, randomly methylated-β-cyclodextrin, ethylated-O-cyclodextrin, triacetyl-O-cyclodextrin, peracetylated-O-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable ophthalmically acceptable chelating agent include those selected from the group consisting of ethylenediaminetetraacetic acid and metal salts thereof, disodium edetate, trisodium edetate, and tetrasodium edetate, and mixtures thereof.

The aqueous vehicle may also include a preservative. Preservatives include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

The topical formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target ophthalmically acceptable pH range. Hence it may not be necessary to use both acid and base—depending on the formulation, the addition of one of the acid or base may be sufficient to bring the mixture to the desired pH range.

The topical formulation may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The topical formulation may further comprise a wetting agent. The wetting agent may be a non-ionic wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

The topical formulation of the present application may also be in the form of a gel or a semi-gel, or both; a jelly; a suspension; an emulsion; an oil; an ointment; a cream; or a spray.

The topical gel, semi-gel, jelly, suspension, emulsion, oil, ointment, cream, or spray may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzalkonium chloride, P-oxybenzoates such as methyl p-oxybenzoate or ethyl p-oxybenzoate, benzyl alcohol, phenethyl alcohol, sorbic acid or its salt, thimerosal, chlorobutanol and the like), solubilizing enhancing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate) and the like.

Furthermore the compounds of the application may be formulated for topical administration by incorporation into topical formulations including but not limited to: microemulsions, liposomes, niosomes, gels, hydrogel, nanoparticles, and nanosuspension.

The compounds of the application may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, and polyethyleneoxidepolylysine substituted with palmitoyl residues. Furthermore, the compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The pharmaceutical compositions can be included in a container, pack, or dispenser together with instructions for administration.

The compounds of the present application are capable of further forming salts. All of these forms are also contemplated within the scope of the claimed application.

As used herein, "pharmaceutically acceptable salts" refer to derivatives of the compounds of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Techniques for formulation and administration of the disclosed compounds of the application can be found in *Remington: the Science and Practice of Pharmacy*, 19th edition, Mack Publishing Co., Easton, Pa. (1995). In an embodiment, the compounds described herein, and the pharmaceutically acceptable salts, tautomers, prodrugs, solvates, metabolites, polymorphs, analogs or derivatives thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds or pharmaceutically acceptable salts, prodrugs, solvates, metabolites, polymorphs, analogs or derivatives thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present disclosure the skilled artisan can identify and employ other components and methodology useful for practicing the present application.

EXAMPLES

Example 1: Synthesis of Vismoister

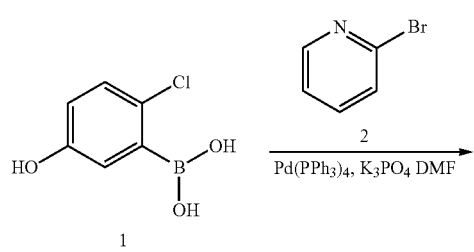

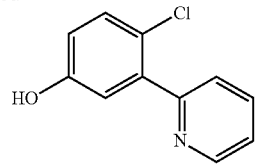

A mixture of 1 (500 mg, 2.9 mmol), 2 (300 g, 2.0 mmol), K₃PO₄ (1.27 mg, 6 mmol) and Pd(PPh₃)₄ (230 mg, 0.2 mmol) in 20 mL of DMF and 5 mL of H₂O was stirred under N2 protection at 80° C. for 17 hours. The reaction mixture was cooled to room temperature, diluted with 100 mL of water and extracted with ethyl acetate (80 mL×3). The combined organic phases were washed brine (100 mL), dried over anhydrous Na₂SO₄ and filtered. The filtrated was concentrated in vacuo. The residue was further purified by reverse flash chromatography (NH₄HCO₃/H₂O:CH₃CN=70:30) to give 3 as yellow solid (220 mg, yield: 53.6%). LC-MS m/z: 206.1 [M+H]⁺. LC-MS Purity (214 nm): >82%; $t_R$=1.447 min.

Synthesis of Vismoister:

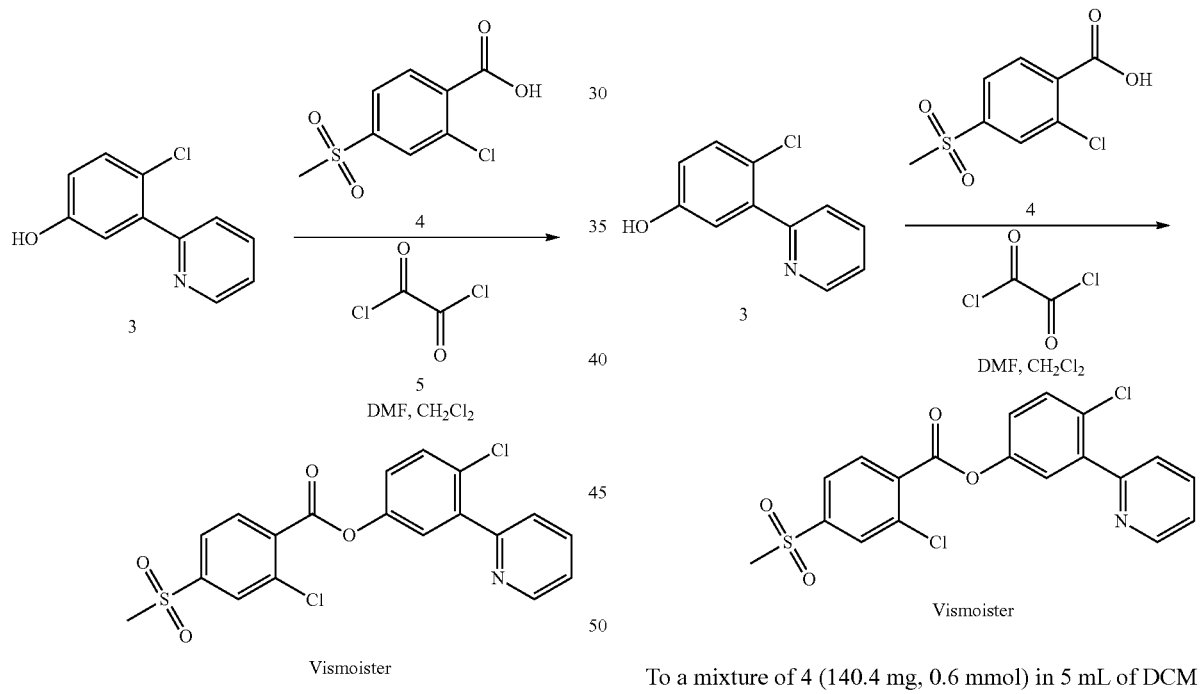

Synthesis of 3:

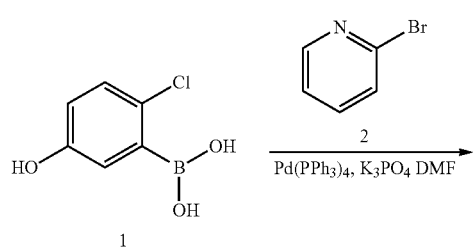

To a mixture of 4 (140.4 mg, 0.6 mmol) in 5 mL of DCM in the presence of DMF (2 drops) at 0° C. was added oxalyl chloride (0.1 mL, 0.72 mmol). Then the mixture was stirred at room temperature for an hour, and a solution of Et₃N (0.3 mL) and 3 (80 mg, 0.4 mmol) in 5 mL of DCM was added. The resulting mixture was stirred at room temperature for 16 hours, and quenched with water (15 mL). The organic phase was separated, and the aqueous phase was extracted with DCM (10 mL×3). The combined organic phases were washed with brine (20 mL), dried over anhydrous Na₂SO₄ and filtered. The filtrated was concentrated in vacuo. The residue was purified by pre-HPLC (TFA) to give Vismoister as white solid (85 mg, yield: 50.3%). LC-MS m/z: 422.0 [M+H]⁺. LC-MS Purity (214 nm): >93%; $t_R$=1.679 min. ¹H NMR (400 MHz, MeOD-d₄): δ 8.75-8.73 (m, 1H), 8.31 (d, J=8.0 Hz, 1H), 8.20 (d, J=2.0 Hz, 1H), 8.15 (dt, J=1.6 Hz, J=8.0 Hz, 1H), 8.08 (dd, J=1.6 Hz, J=8.0 Hz, 1H), 7.88-7.85 (m, 1H), 7.72 (d, J=8.8 Hz, 1H), 7.66-7.63 (m, 1H), 7.58 (d, J=2.8 Hz, 1H), 7.50 (dd, J=2.8 Hz, J=8.8 Hz, 1H), 3.25 (s, 3H).

Example 2: Synthesis of LY-Ester

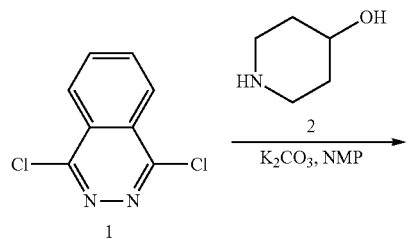

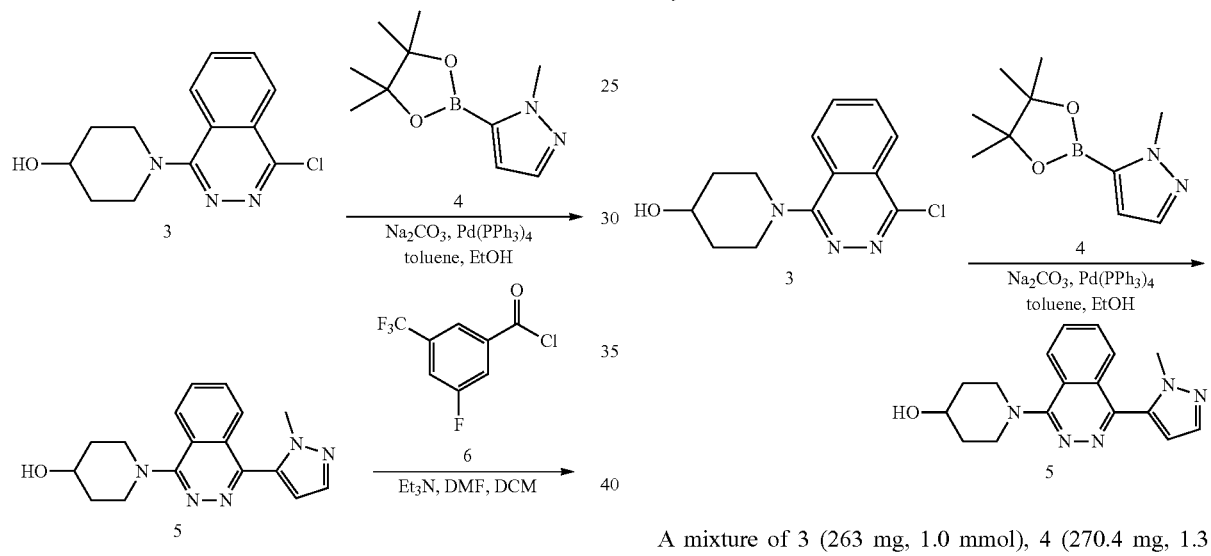

Synthesis of 3:

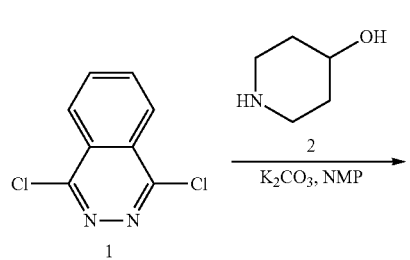

-continued

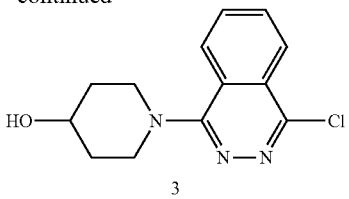

A mixture of 1 (533 mg, 5.3 mmol), 2 (1 g, 5.02 mmol) and K$_2$CO$_3$ (828 mg, 6 mmol) in 10 mL of NMP was stirred at 80° C. for 17 hours. The reaction mixture was diluted with water (50 mL) and extracted with dichloromethane (40 mL×3). The combined organic phases were washed with brine (50 mL), dried over anhydrous Na$_2$SO$_4$, and filtered. The filtrate was concentrated in vacuo. The residue was purified by silica gel column (ethyl acetate:petroleum ether=1:4) to give 3 as white solid (1.2 g, yield: 91.25%). LC-MS m/z: 264.1 [M+H]$^+$. LC-MS Purity (214 nm): > 94%; t$_R$=1.475 min.

Synthesis of 5:

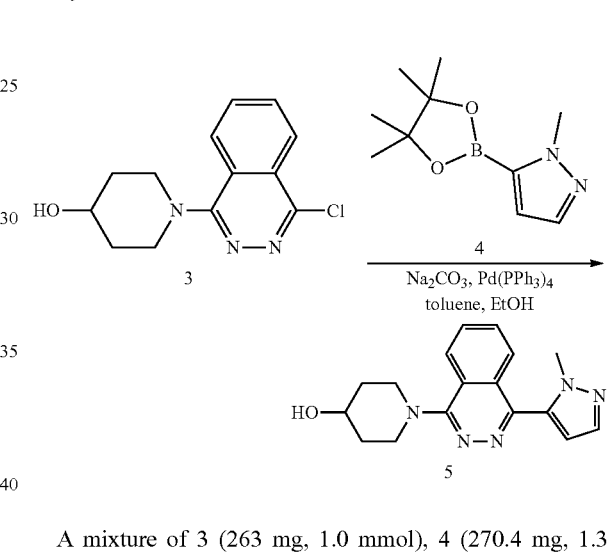

A mixture of 3 (263 mg, 1.0 mmol), 4 (270.4 mg, 1.3 mmol), Na$_2$CO$_3$ (212 mg, 2 mmol) and Pd(PPh$_3$)$_4$ (57.7 mg, 0.05 mmol) in toluene (10 mL), EtOH (3 mL) and H$_2$O (3 mL) was stirred at 75° C. for 17 hours. The reaction mixture was cooled to room temperature, diluted with water (40 mL) and extracted with dichloromethane (30 mL×3). The combined organic phases were washed with brine (50 mL), dried over anhydrous Na$_2$SO$_4$ and filtered. The filtrate was concentrated in vacuo. The residue was purified by silica gel column (DCM:MeOH=95:5) to give 5 as red solid (220 mg, yield: 70.1%). LC-MS m/z: 310.2 [M+H]$^+$. LC-MS Purity (214 nm): >96%; t$_R$=1.255 min.

Synthesis of LY-Ester:

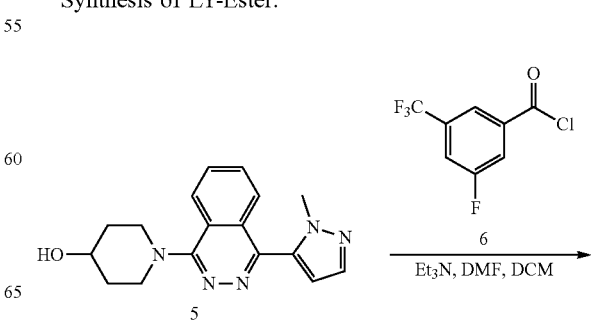

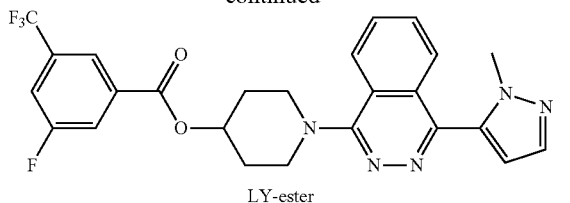

LY-ester

To a stirred solution of 5 (62 mg, 0.2 mmol) and Et₃N (0.1 ml, 0.6 mmol) in 5 mL of dichloromethane was added 6 (68 mg, 0.3 mmol). Then the mixture was stirred at room temperature for 17 hours and quenched with water (10 mL). The organic phase was separated, and the aqueous phase was extracted with dichloromethane (10 mL×3). The combined organic phases were washed with brine (20 mL), dried over anhydrous Na₂SO₄ and filtered. The filtrate was concentrated in vacuo. The residue was purified by silica gel column (ethyl acetate:petroleum ether=1:1) to give LY-ester as white solid (66 mg, yield: 66.1%). LC-MS m/z: 500.1 [M+H]⁺. LC-MS Purity (214 nm): >98%; $t_R$=1.726 min. ¹H NMR (400 MHz, CDCl₃): δ 8.14-8.09 (m, 3H), 7.98 (d, J=8.8 Hz, 1H), 7.93-7.84 (m, 2H), 7.68 (d, J=2.0 Hz, 1H), 7.57 (d, J=8.4 Hz, 1H), 6.61 (d, J=2.0 Hz, 1H), 5.45-5.39 (m, 1H), 4.08 (s, 3H), 3.99-3.93 (m, 2H), 3.64-3.58 (m, 2H), 2.38-2.33 (m, 2H), 2.25-2.16 (m, 2H).

Example 3: Synthesis of Erismoester

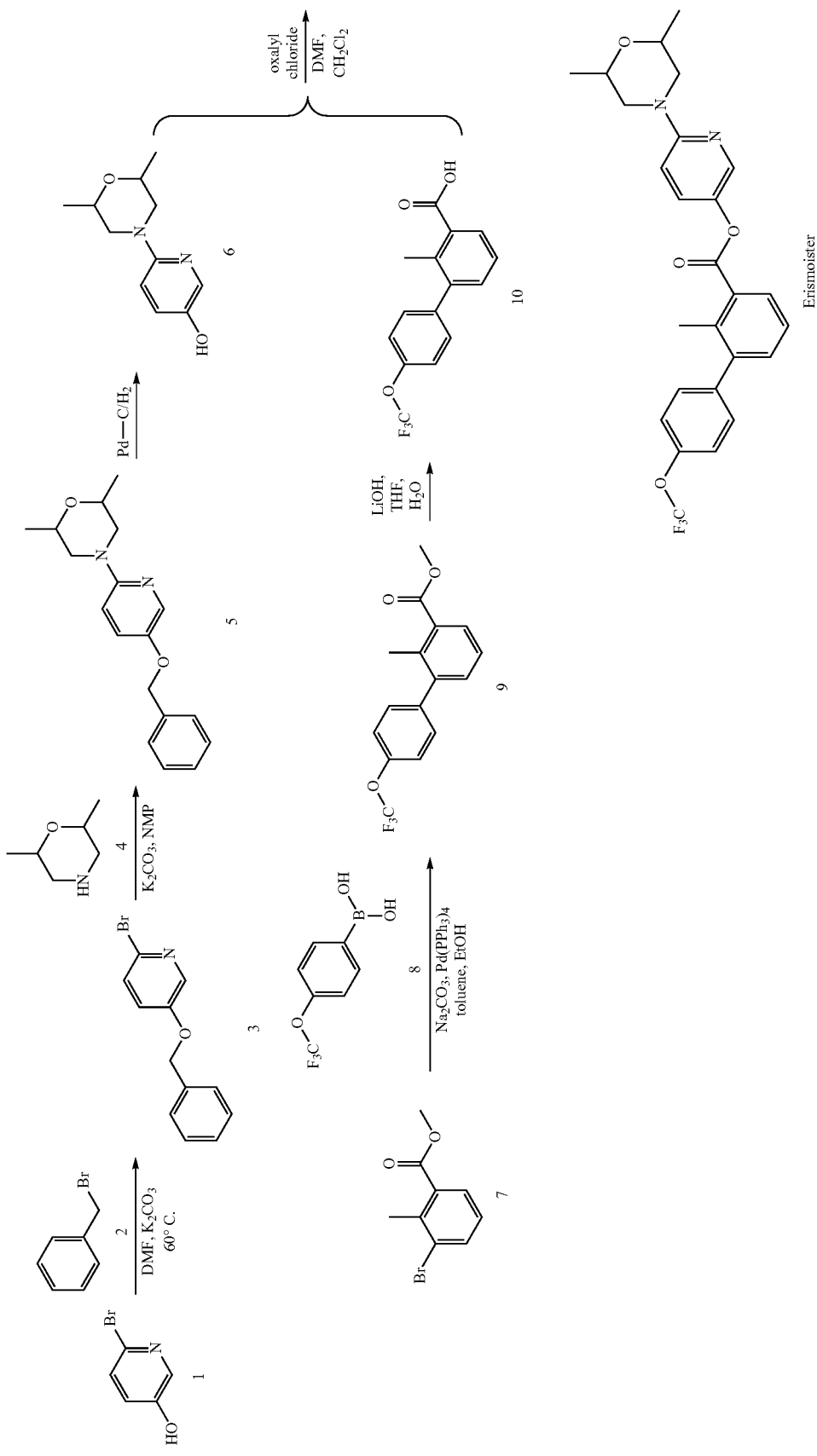

Synthesis of 3:

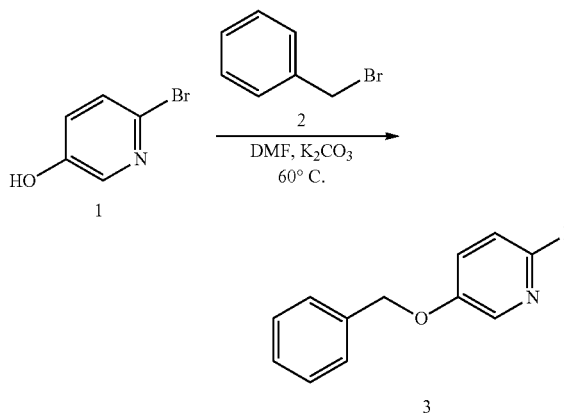

A mixture of 2 (579 mg, 3.46 mmol), 1 (500 mg, 2.89 mmol) and K$_2$CO$_3$ (1.2 mg, 8.7 mmol) in 5 mL of DMF was stirred at 60° C. for 16 hours. The reaction mixture was diluted with water (50 mL) and extracted with ethyl acetate (40 mL×3). The combined organic phases were washed with water (50 mL), brine (50 mL), dried over anhydrous Na$_2$SO$_4$ and filtered. The filtration was concentrated in vacuo, and the residue was purified by silica gel chromatography (ethyl acetate:petroleum ether=10:1) to give 3 as white solid (650 mg, yield: 85.5%). LC-MS m/z: 266.0 [M+H]$^+$. LC-MS Purity (254 nm): >81%; $t_R$=1.964 min.

Synthesis of 5:

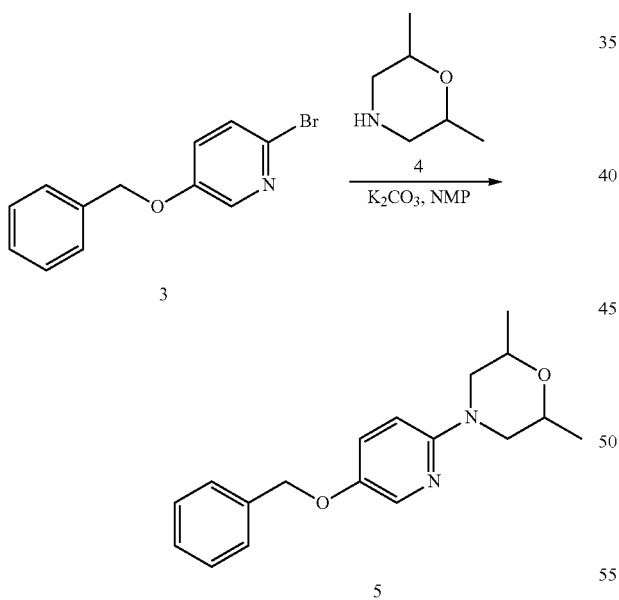

A mixture of 3 (500 mg, 1.9 mmol), 4 (262 mg, 2.3 mmol), t-BuOK (851 mg, 7.6 mmol), Pd$_2$(dba)$_3$ (174 mg, 0.19 mmol) and BINAP (355 mg, 0.57 mmol) in 15 mL of toluene was stirred under N2 protection at 80° C. for 17 hours. The mixture was filtered through celite, and the filtrate was concentrated in vacuo. The residue was purified by reverse flash chromatography eluted with (NH$_4$HCO$_3$/H$_2$O:CH$_3$CN=36:64) to give 5 as brown oil (260 mg, yield: 45.9%). LC-MS m/z: 299.7 [M+H]$^+$. LC-MS Purity (214 nm): >83%; $t_R$=1.998 min.

Synthesis of 6:

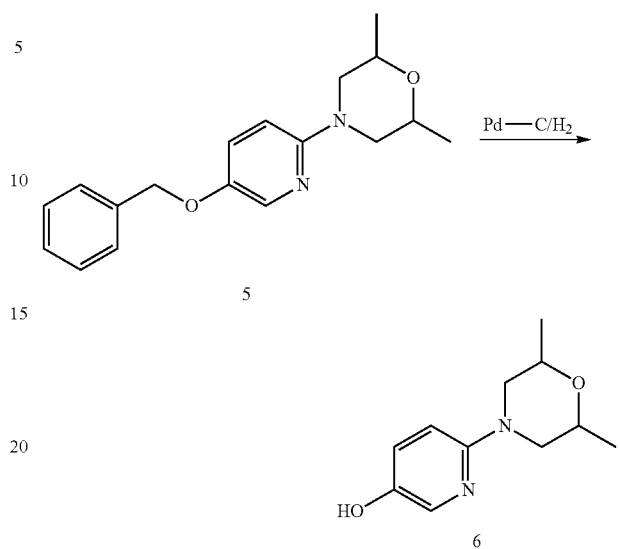

A mixture of 5 (250 mg, 0.83 mmol) and 10% Pd/C (15 mg) in 10 mL of methanol was stirred under H$_2$ (1 atm) for 2 hours. The reaction mixture was filtered through celite, and the filtrate was concentrated in vacuo to give 6 as oil (160 mg, yield: 92.6%).

Synthesis of 9:

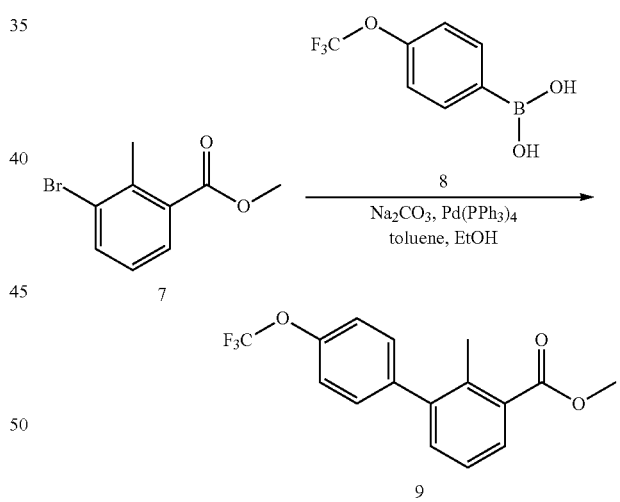

A mixture of 7 (228 mg, 1.0 mmol), 8 (288 mg, 1.4 mmol), Na$_2$CO$_3$ (212 mg, 2 mmol) and Pd(PPh$_3$)$_4$(115 mg, 0.10 mmol) in 2 mL of toluene, 2 mL of ethanol and 2 mL of water was stirred under N$_2$ protection at 80° C. for 17 hours concentrated in vacuo. The residue was diluted with ethyl acetate (50 mL), washed with water (30 mL) and brine (30 mL), dried over anhydrous Na$_2$SO$_4$ and filtered. The filtrate was concentrated in vacuo and the residue was purified by silica gel chromatography (ethyl acetate:petroleum ether=1:50) to give 9 as white oil (260 mg, yield: 83.8%). LC-MS m/z: 311.1 [M+H]$^+$. LC-MS Purity (214 nm): >96%; $t_R$=2.256 min.

Synthesis of 10:

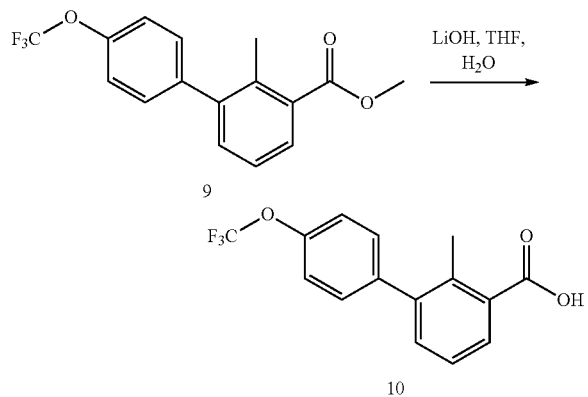

A mixture of 9 (260 mg, 0.84 mmol), LiOH.H$_2$O (211 mg, 5 mmol) in 3 mL of THF, 1 mL of methanol and 1 mL of water was stirred at room temperature for 16 hours, and concentrated in vacuo. The residue was diluted with water (2 mL), acidified with 1M HCl until pH~3. The suspension was filtered to give 10 as white solid (247 mg, 0.99%). LC-MS m/z: 297.1 [M+H]$^+$. $^1$H NMR (400 MHz, CDCl$_3$): δ 8.06-8.04 (m, 1H), 7.44-7.41 (m, 1H), 7.38-7.28 (m, 5H), 2.51 (s, 3H).

Synthesis of Erismoester:

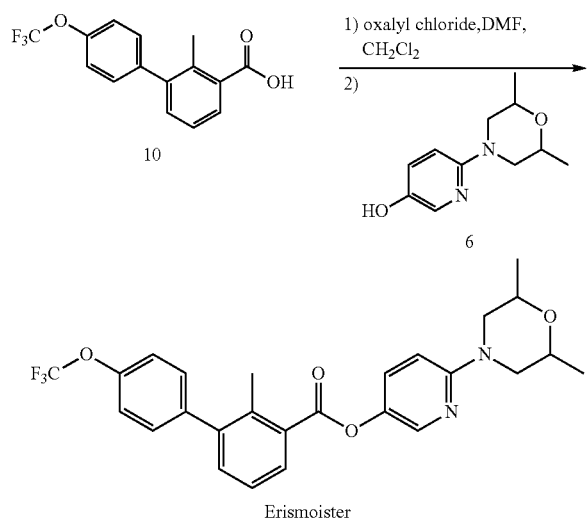

Erismoister

To a mixture of 10 (80 mg, 0.27 mmol) in 3 mL of DCM in the presence of DMF (1 drop) at 0° C. was added oxalyl chloride (0.04 mL, 0.4 mmol). Then the mixture was stirred at room temperature for 2 hours, and a solution of Et$_3$N (0.1 ml, 0.8 mmol) and 6 (40 mg, 0.2 mmol) in 5 mL of DCM was added. The resulting mixture was stirred at room temperature for 2.5 hours, diluted with DCM (20 mL) and washed with water (15 mL). The organic phase was washed with brine (20 mL), dried over anhydrous Na$_2$SO$_4$ and filtered. The filtrate was concentrated in vacuo. The residue was purified by pre-HPLC (TFA) to give Erismoister as brown oil (80 mg, yield: 82%). LC-MS m/z: 487.1 [M+H]$^+$. LC-MS Purity (214 nm): >99%; t$_R$=2.374 min. $^1$H NMR (400 MHz, CDCl$_3$): δ 8.14-8.11 (m, 2H), 7.47-7.28 (m, 7H), 6.71 (d, J=9.6 Hz, 1H), 4.06-4.02 (m, 2H), 3.79-3.75 (m, 2H), 2.60-2.54 (m, 2H), 2.50 (s, 3H), 1.30-1.28 (m, 6H).

Example 4: Biological Assays

Stability Measurements

SMO antagonists were incubated at 250 µM (vismodegib, vismo-ester, erismodegib, erismo-ester) or 25 µM (LY2940680, LY-ester) in human serum or serum-free cell culture media at 37° C. for varying lengths of time by adding 5 µL of SMO antagonist (10 or 1 mM) to 195 µL of serum or media. Reactions were terminated by adding 600 µL of cold acetonitrile. Samples were centrifuged at 1000×g for 15 min at 4° C. and the supernatant was removed, passed through a 0.22 µm filter, and measured by LC-MS. The percent remaining of each compound was calculated by the integrated area of the peak at each time point divided by the peak at the t=0 time point. Data was fit to a one-phase decay curve using GraphPad Prism 6 software.

Figure 2:
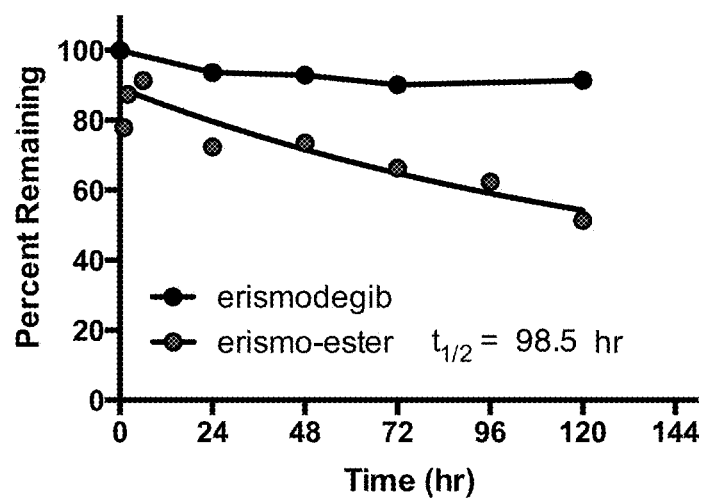
FIG. 2: a graph showing the amount of erismoester incubated at 37° C. in serum over time.
Figure 3:
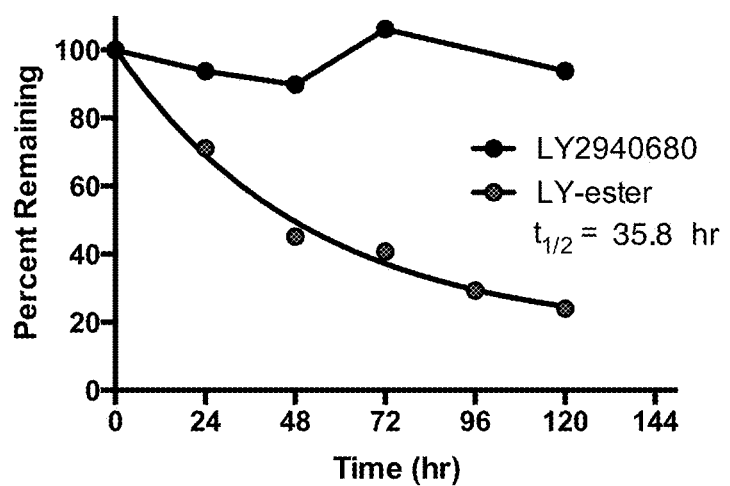
FIG. 3: a graph showing the amount of LY-ester incubated at 37° C. in serum over time.

The percent remaining of each compound is shown in FIG. 1 (vismo-ester in comparison with vismodegib), FIG. 2 (erismo-ester in comparison with erismodegib), and FIG. 3 (LY-ester in comparison with LY2940680).

Cell Viability

SmoWT-MB cells are a mouse medulloblastoma cell line with wild-type Smo and Ptch1 loss of function. SmoWT-MB cells were distributed into 384-well plates at 1000 cells per well in a total volume of 50 µL and then pinned with 100 nL of SMO antagonists in quadruplicate over a ten-point dose range. Cell viability, relative to DMSO treated cells, was measured after 24, 48, 72, or 96 hours by ATPlite and IC$_{50}$ was determined by fitting dose-response curves in GraphPad Prism 6 software.

Figure 4:
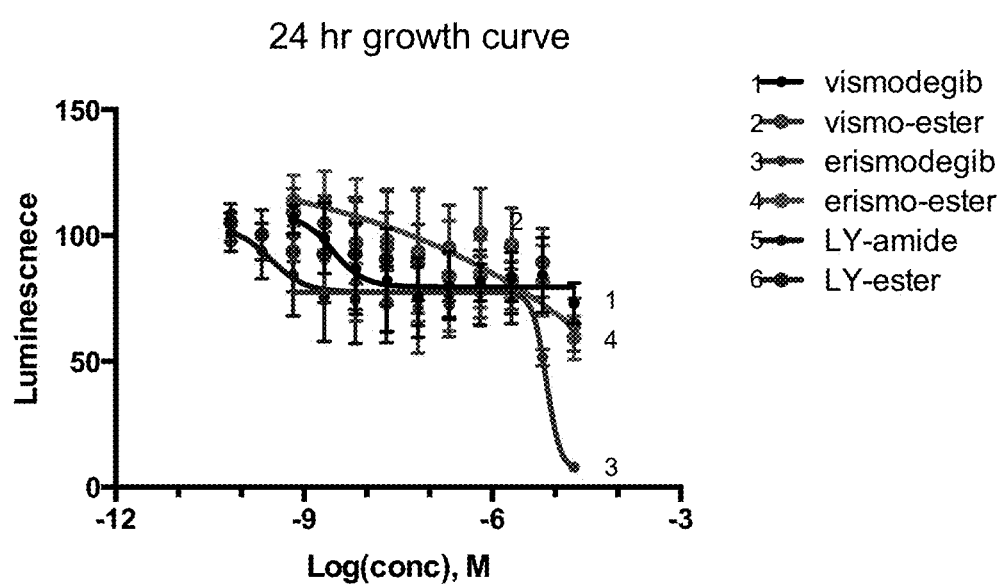
FIG. 4: a graph showing the number of viable mouse medulloblastoma cells (indicated as relative luminescence) 24 hours after treatment of the cells with increasing concentrations of the indicated compounds.
Figure 5:
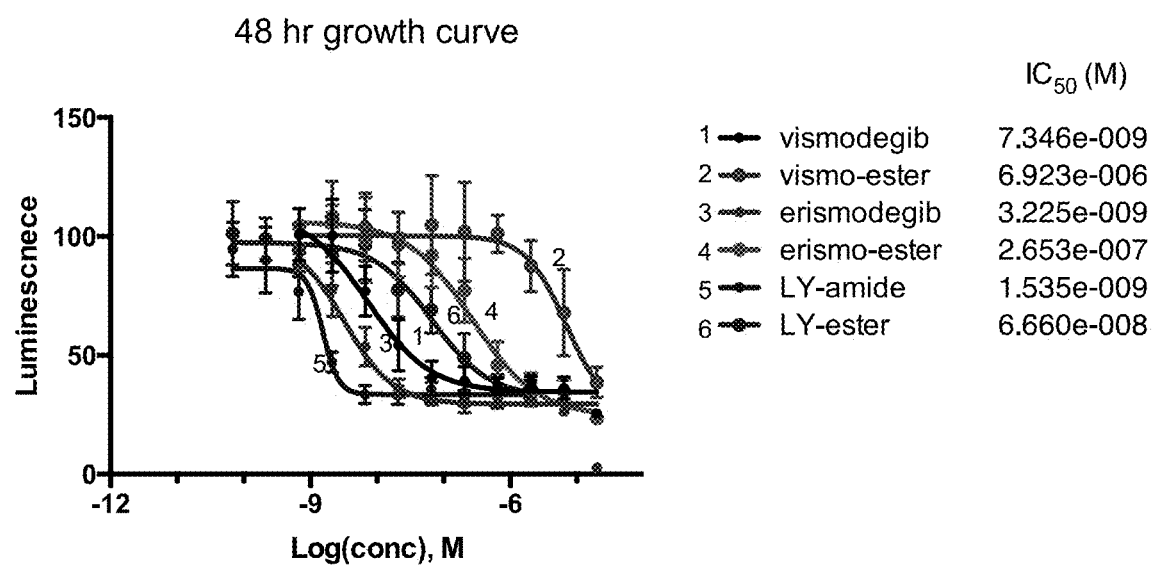
FIG. 5: a graph showing the number of viable mouse medulloblastoma cells (indicated as relative luminescence) 48 hours after treatment of the cells with increasing concentrations of the indicated compounds.
Figure 6:
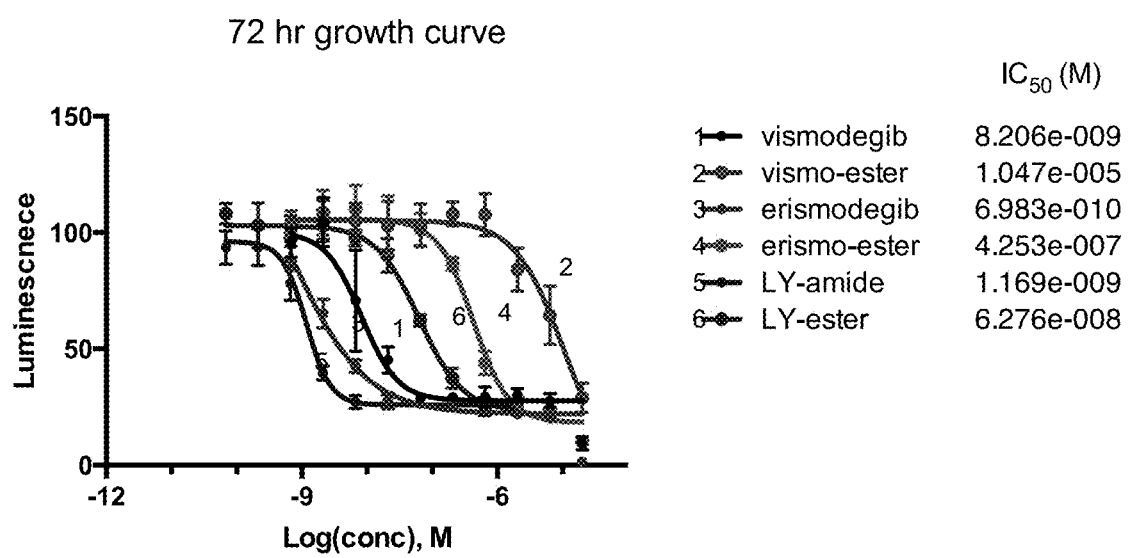
FIG. 6: a graph showing the number of viable mouse medulloblastoma cells (indicated as relative luminescence) 72 hours after treatment of the cells with increasing concentrations of the indicated compounds.
Figure 7:
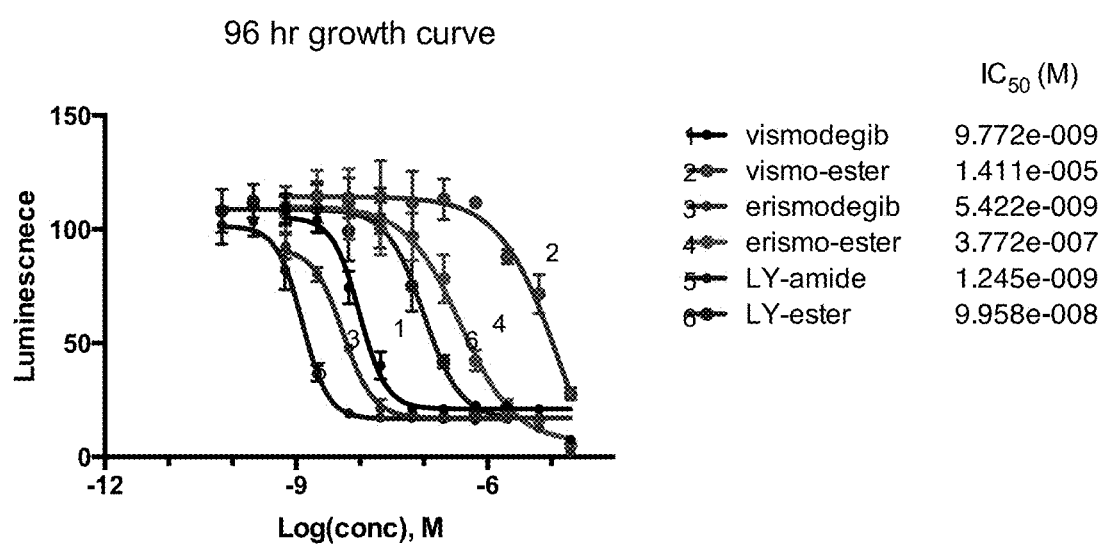
FIG. 7: a graph showing the number of viable mouse medulloblastoma cells (indicated as relative luminescence) 96 hours after treatment of the cells with increasing concentrations of the indicated compounds.

The viability of cells (indicated by the relative luminescence intensity) is shown in FIG. 4 (24 hour), FIG. 5 (48 hours), FIG. 6 (72 hours), and FIG. 7 (96 hours).

Gene Expression Analysis

SmoWT-MB cells were plated at 250,000 cells per well in 6-well tissue culture plates, grown for 24 hours, and treated with 1 µM SMO antagonists or DMSO for 24 hours. After treatment, RNA was extracted from cells using the RNeasy kit (Qiagen) and cDNA was prepared from 1 µg RNA using the SuperScript cDNA synthesis kit. The fold-change in expression for Gli1 and Ptch1, relative to DMSO treatment and normalized by Hprt, was determined by qRT-PCR using the ΔΔC$_t$ method.

Figure 8:
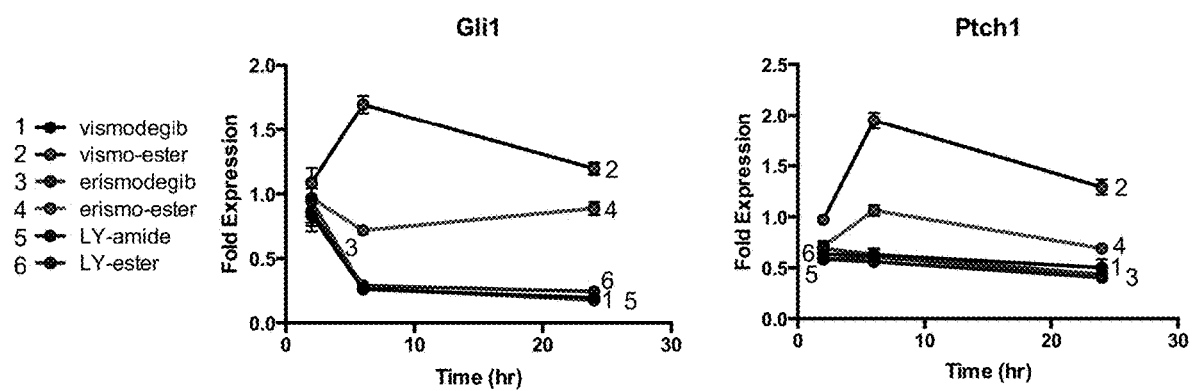
FIG. 8: graphs showing the expression of Hh target genes (Gli1 (left panel) and Ptch 1 (right panel)) in mouse medulloblastoma cells 24 hours after treatment of the cells with 1 μM of the indicated compounds.
Figure 9:
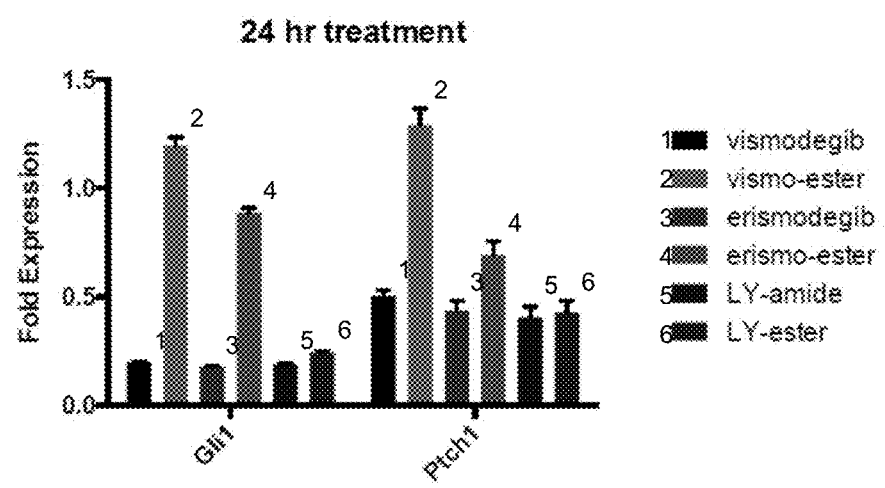
FIG. 9: bar graphs showing the expression of Hh target genes in mouse medulloblastoma cells at various time points after treatment of the cells with 1 μM of the indicated compounds.

The fold change in expression of Gli1 and Ptch 1 is shown in FIGS. 8 and 9.

Hh Pathway Cell Reporter Assays

Shh-LightII cells (NIH-3T3 cells stably expressing Gli-dependent firefly luciferase and constitutively active *Renilla* luciferase) were distributed into 24-well tissue culture plates at 150,000 cells per well and grown for 48 hours. Cells were changed to serum-free media and Hh pathway activity was stimulated by 20 nM treatment with Smoothened agonist (SAG). Cells were treated with 10 µM smoothened antagonist for 24 hours (or for 24 hours with an additional dose after 20 hours) and luciferase activity (normalized to *Renilla* luciferase and relative to DMSO treated cells) was measured using the Dual Luciferase Reporter Assay kit (Promega) as a surrogate for Hh pathway activation.

Figure 10:
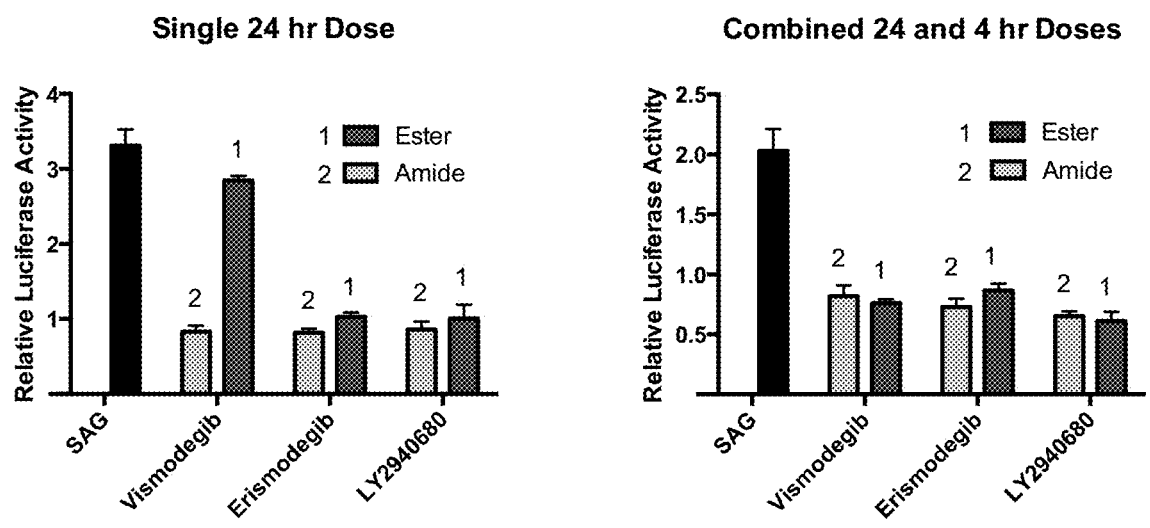
FIG. 10: bar graphs showing the expression of Hh target genes (indicated as relative luciferase activity) in Shh-Light2 cells (NIH/3T3 cells stably expressing Hh responsive firefly luciferase) 24 hours after treatment of the cells with the indicated compounds. Left panel: the cells were treated once with 20 nM Smoothened Agonist (SAG) or 10 μM of the indicated compounds. Right panel: the cells were treated twice (at 0 hr and at 20 hr) with 20 nM Smoothened Agonist (SAG) or 10 μM of the indicated compounds.

The reporter expression (indicated by the relative luciferase activity) as modulated by vismo-ester vs. vismodegib, by erismo-ester vs. erismodegib, or by LY-ester vs. LY2940680 is shown in FIG. 10.

The invention claimed is:

1. A compound having formula II:

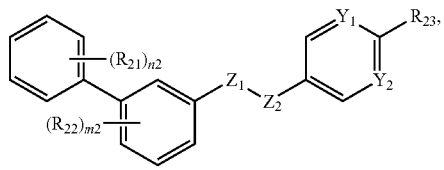

or a pharmaceutically acceptable salt thereof, wherein:
$Z_1$-$Z_2$ is C(O)—O, O—C(O), C(O)—S, S—C(O), C(O)—NR—NR, or NR—NR—C(O);
$Y_1$ is N and $Y_2$ is N or $CR_{24}$;
each $R_{24}$ is independently H, halogen, cyano, unsubstituted or substituted $C_1$-$C_6$ alkyl, or unsubstituted or substituted $C_1$-$C_6$ alkoxy;
n2 is 0, 1, 2, 3, 4, or 5;
each $R_{21}$ is independently halogen, cyano, unsubstituted or substituted $C_1$-$C_6$ alkyl, unsubstituted or substituted $C_1$-$C_6$ alkoxy, S(O)$_{o2}$-(unsubstituted or substituted $C_1$-$C_6$ alkyl), amino, di-$C_1$-$C_6$ alkylamino, or unsubstituted or substituted $C_6$-$C_{10}$ aryl;
o2 is 0, 1, or 2;
m2 is 0, 1, 2, 3, or 4;
each $R_{22}$ is independently halogen, unsubstituted or substituted $C_1$-$C_6$ alkyl, or unsubstituted or substituted $C_1$-$C_6$ alkoxy;
$R_{23}$ is $R_{25}$, S(O)$_2R_{25}$, C(O)$R_{25}$, $OR_{25}$, or $NR_{26}R_{27}$;
$R_{25}$ is unsubstituted or substituted $C_3$-$C_8$ cycloalkyl, unsubstituted or substituted $C_6$-$C_{10}$ aryl, unsubstituted or substituted heterocyclyl comprising one or two 5- to 8-membered rings and 1-4 heteroatoms selected from O, N, and S, or unsubstituted or substituted heteroaryl comprising one or two 5- to 8-membered rings and 1-4 heteroatoms selected from O, N, and S; and
$R_{26}$ and $R_{27}$ are each independently H or unsubstituted or substituted $C_1$-$C_6$ alkyl.

2. The compound of claim 1, having formula IIa:

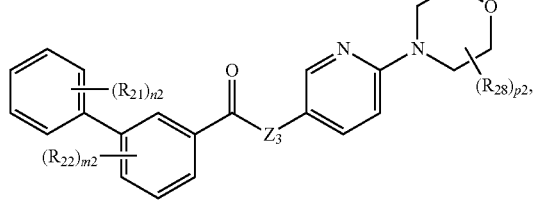

or a pharmaceutically acceptable salt thereof, wherein:
$Z_3$ is O, S, or NR—NR;
p2 is 0, 1, 2, 3, or 4; and
each $R_{28}$ is independently unsubstituted or substituted $C_1$-$C_6$ alkyl.

3. A pharmaceutical composition comprising the compound of claim 1 or a pharmaceutically acceptable salt thereof, and a pharmaceutically acceptable carrier.

4. A method of modulating the SMO, comprising contacting the SMO with the compound of claim 1 or a pharmaceutically acceptable salt thereof.

5. A method of treating a disorder mediated by the Hedgehog (Hh) signaling pathway, comprising administering to a subject in need thereof, a therapeutically effective amount of the compound of claim 1, or a pharmaceutically acceptable salt thereof.

6. The compound of claim 1, wherein $Y_2$ is $CR_{24}$.
7. The compound of claim 6, wherein $R_{24}$ is H.
8. The compound of claim 1, wherein $n_2$ is 1.
9. The compound of claim 1, wherein $R_{21}$ is unsubstituted or substituted straight-chain $C_1$-$C_6$ alkoxy.
10. The compound of claim 9, wherein $R_{21}$ is trifluoromethoxy.
11. The compound of claim 1, wherein $m_2$ is 1.
12. The compound of claim 1, wherein $R_{22}$ is unsubstituted or substituted straight-chain $C_1$-$C_6$ alkyl.
13. The compound of claim 12, wherein $R_{22}$ is methyl.
14. The compound of claim 1, wherein $R_{23}$ is heterocyclyl optionally substituted with one or more substituents independently selected from halogen, OH, cyano, nitro, $C_1$-$C_6$ alkyl, $C_1$-$C_6$ alkoxy, and amino.
15. The compound of claim 14, wherein $R_{23}$ is morpholinyl substituted with two substituents independently selected from methyl, ethyl, and propyl.
16. The compound of claim 1, which is:

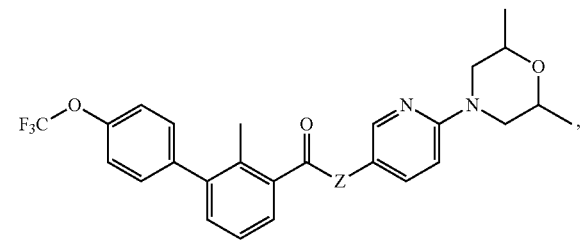

or a pharmaceutically acceptable salt thereof, wherein Z is O, S, or NH—NH.

17. The compound of claim 16, which is:

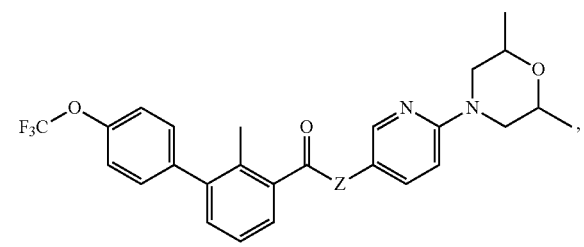

or a pharmaceutically acceptable salt thereof, wherein Z is O.

18. The compound of claim 1, which is:

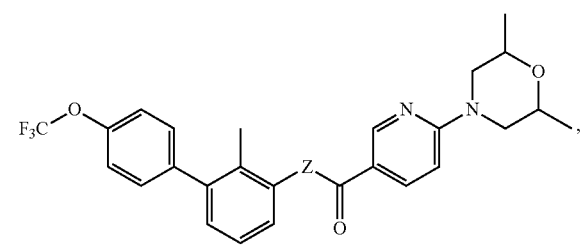

or a pharmaceutically acceptable salt thereof, wherein Z is O, S, or NH—NH.

* * * * *